US008969001B2

(12) United States Patent
Buckingham

(10) Patent No.: US 8,969,001 B2
(45) Date of Patent: Mar. 3, 2015

(54) MATERIALS AND METHODS FOR PREDICTING RECURRENCE OF NON-SMALL CELL LUNG CANCER

(75) Inventor: Lela Buckingham, Kenosha, WI (US)

(73) Assignee: Rush University Medical Center, Chicago, IL (US)

( * ) Notice: Subject to any disclaimer, the term of this patent is extended or adjusted under 35 U.S.C. 154(b) by 672 days.

(21) Appl. No.: 12/721,742

(22) Filed: Mar. 11, 2010

(65) Prior Publication Data
US 2010/0233707 A1  Sep. 16, 2010

Related U.S. Application Data

(60) Provisional application No. 61/159,743, filed on Mar. 12, 2009.

(51) Int. Cl.
*C12Q 1/68* (2006.01)

(52) U.S. Cl.
CPC ........ *C12Q 1/6886* (2013.01); *C12Q 2600/118* (2013.01); *C12Q 2600/154* (2013.01)
USPC ......................................................... 435/6.1

(58) Field of Classification Search
None
See application file for complete search history.

(56) References Cited

U.S. PATENT DOCUMENTS

| | | | |
|---|---|---|---|
| 2004/0086944 A1 | 5/2004 | Grigg et al. | |
| 2004/0219539 A1 | 11/2004 | Millar et al. | |
| 2007/0020633 A1 | 1/2007 | Millar et al. | |

OTHER PUBLICATIONS

Brock et al. (NEJM, 2008, 358: 1118-28).*
Friederich et al. (European Journal of Cancer, 2005, vol. 41, p. 2769-2778, IDS reference).*
van Engeland et al. (Cancer Research, 2003, 63:3133-7).*
Kim et al. (Cancer Res, 2003, 63:3743-3746).*
Buckingham et al. (Journal of Clin Oncology, 2008, vol. 26, No. 15S, 11035, Abstract).*
Soria et al. (Clin Cancer Res, 2002, 8:1178-84).*
Tomizawa et al. (Clin Cancer Res., 2002, 8:2362-2368).*
Burbee et al. (JNCI, 2001, p. 691-699).*
Marsit et al. (Human Pathology, 2005, 36:768-776).*
Belinsky et al., "Aberrant Promoter Methylation in Bronchial Epithelium and Sputum from Current and Former Smokers," Cancer Research, vol. 62, Apr. 15, 2002, pp. 2370-2377.
Blanco et al., "Molecular Analysis of a Multistep Lung Cancer Model Induced by Chronic Inflammation Reveals Epigenetic Regulation of p16 and Activation of the DNA Damage Response Pathway," Neoplasia, vol. 9, No. 10, Oct. 2007, pp. 840-852.
Brock et al., "DNA methylation markers and early recurrence in stage I lung cancer," New England Journal of Medicine, vol. 358, No. 11, 2008, pp. 1118-1128.
Buckingham et al., "Molecular Diagnostics, Fundamentals, Methods & Clinical Applications," F.A. Davis Co., 2007, pp. 65-70.

Buckingham et al., "The prognostic value of chromosome 7 polysomy in non-small cell lung cancer patients treated with gefitinib," J Thoracic Onoc, May 2007, vol. 2, No. 5, pp. 414-422.
Burbee et al., "Epigenetic inactivation of RASSF1A in lung and breast cancers and malignant phenotype suppression," Journal of the National Cancer Institute, vol. 93, No. 9, May 2, 2001, pp. 691-699.
Clark et al., "High sensitivity mapping of methylated cytosines," Nucl Acids Res, vol. 22, No. 15, 1994, pp. 2290-2297.
De Jong et al., "Promoter Methylation Primarily Occurs in Tumor Cells of Patients with Non-small Cell Lung Cancer," Anticancer Research, vol. 29, No. 1, Jan. 2009, pp. 363-370.
Esteller, "Epigenetics in Cancer," N Engl J Med, 2008, vol. 358, No. 11, Mar. 13, 2008, pp. 1148-1159.
Friedrich et al., "Prognostic relevance of methylation markers in patients with non-muscle invasive bladder carcinoma," Eur J Cancer, Nov. 2005, vol. 41, No. 17, pp. 2769-2778.
Frommer et al., "A genomic sequencing protocol that yields a positive display of 5-methylcytosine residues in individual DNA strands," PNAS 89, 1992, pp. 1827-1831.
Fukami et al., "Promoter methylation of the TSLC1 gene in advanced lung tumors and various cancer cell lines," Int J Cancer, Oct. 20, 2003, vol. 107, No. 1, pp. 53-59.
Grote et al., "Methylation of RAS association domain family protein 1A as a biomarker of lung cancer," Cancer, vol. 108, No. 2, Apr. 25, 2006, pp. 129-134.
Herman et al., "Methylation-Specific PCR," Current Protocols in Human Genetics, 1998, 2:10.6.1-10.6.10, 10 pages.
Herman et al., "Methylation-specific PCR: a novel PCR assay for methylation status of CpG islands," Proc. Natl. Acad. Sci., Sep. 1996, vol. 93, pp. 9821-9826.
Jarmalaite et al., "Aberrant p16 promoter methylation in smokers and former smokers with nonsmall cell lung cancer," Int J Cancer, Oct. 10, 2003, vol. 106, No. 6, pp. 913-918.
Kim et al., "Aberrant methylation of E-cadherin and H-cadherin genes in nonsmall cell lung cancer and its relation to clinicopathologic features," Cancer, Dec. 15, 2007, vol. 110 No. 12, pp. 2785-2792.
Kim et al., "Can Aberrant Promoter Hypermethylation of CpG Islands Predict the Clinical Outcome of Non-Small Cell Lung Cancer After Curative Resection?," The Annals of Thoracic Surgery, vol. 79, No. 4, Apr. 2005, pp. 1180-1188.
Kim et al., "Cohypermethylation of p16 and FHIT promoters as a prognostic factor of recurrence in surgically treated resected stage 1 non-small cell lung cancer," Cancer Research, vol. 66, No. 8, Apr. 15, 2006, pp. 4049-4054.

(Continued)

*Primary Examiner* — Stephanie K Mummert
(74) *Attorney, Agent, or Firm* — McDermott Will & Emery LLP

(57) ABSTRACT

Disclosed herein is a DNA methylation-based test for determining the recurrence or non-recurrence of a lung cancer such as NSCLC after treatment. The assays involve the detection of methylation of the BAX gene promoter alone or in combination with other genes. The test is suitable for monitoring treatment of subjects with lung cancer for which methylation differs by stage of the disease and by treatment regimen.

18 Claims, 9 Drawing Sheets

(56) References Cited

OTHER PUBLICATIONS

Kim et al., "Elevated mRNA levels of DNA methyllransferase-1 as an independent prognostic factor in primary nonsmall cell lung cancer," Cancer, vol. 107, No. 5, Sep. 1, 2006, 1042-1049.

Kim et al., "Hypermethylation of RASSF1A Promoter Is Associated with the Age at Starting Smoking and a Poor Prognosis in Primary Non-Small Cell Lung Cancer," Cancer Research, vol. 63, Jul. 1, 2003, pp. 3743-3746.

Krauntz et al., "Homozygous deletion of p16INK4a and tobacco carcinogen exposure in nonsmall cell lung cancer," Int J Cancer, Mar. 15, 2006, vol. 118, No. 6, pp. 1364-1369.

Marsit et al., "Genetic and Epigenetic Tumor Suppressor Gene Silencing Are Distinct Molecular Phenotypes Driven by Growth Promoting Mutations in Nonsmall Cell Lung Cancer," Journal of Cancer Epidemiology, vol. 2008, Article ID 215809, 8 pages.

Niklinska et al., "Prognostic signifigance of DAPK and RASSF1A promoter hypermethylation in Non-Small Cell Lung Cancer (NSCLC)," Folia Histochem Cytobio, vol. 47, No. 2, 2009, pp. 275-280.

Reinhold et al., "Detailed DNA methylation profiles of the E-cadherin promoter in the NCI-60 cancer cells," Mol Cancer Ther, vol. 6, No. 2, Feb. 2007, pp. 391-403.

Russo et al., "Differential DNA Hypermethylation of Critical Genes Mediates the Stage-Specific Tobacco Smoke-Induced Neoplastic Progression of Lung Cancer," Clinical Cancer Research, vol. 11, No. 7, Apr. 1, 2005, pp. 2466-2470.

Shaw et al., "Promoter methylation of P16, RARbeta, E-cadherin, cyclin A1 and cytoglobin in oral cancer: quantitative evaluation using pyrosequencing," Br J Cancer, Feb. 27, 2006, vol. 94 No. 4, pp. 561-568.

Tomizawa et al., "Clinicopathological Signifigance of Epigenetic Inactivation of RASSF1A at 3p21.3 in Stage I Lung Adenocarcinoma," Clincal Cancer Research, vol. 8, Jul. 2002, pp. 2362-2368.

Vaissie'Re et al., "Quantitative Analysis of DNA Methylation Profiles in Lung Cancer Identifies Aberrant DNA Methylation of Specific Genes and Its Association with Gender and Cancer Risk Factors," Cancer Research, vol. 69, No. 1, Jan. 1, 2009, pp. 243-252.

Vos et al., "The RASSF1A Tumor Suppressor Activates Bax via MOAP-1," J Biol Chem, vol. 281, No. 8, Feb. 24, 2006, pp. 4557-4563.

Yoshino et al., "Promoter hypermethylation of the p16 and Wif-1 genes as an independent prognostic marker in stage IA non-small cell lung cancers," Int J Oncol., vol. 35, No. 5, Nov. 2009, pp. 1201-1209.

Zhang "Association of DNA methylation and epigenetic inactivation of RASSF1A and beta-catenin with metastasis in small bowel carcinoid tumors," Endocrine, vol. 30, No. 3, Dec. 2006, pp. 299-306.

Buckingham et al., "PTEN, RASSF1 and DAPK site-specific hypermethylation and outcome in surgically treated stage I and II nonsmall cell lung cancer patients," Int J Cancer, Apr. 1, 2010, vol. 126, No. 7, pp. 1630-1639.

\* cited by examiner

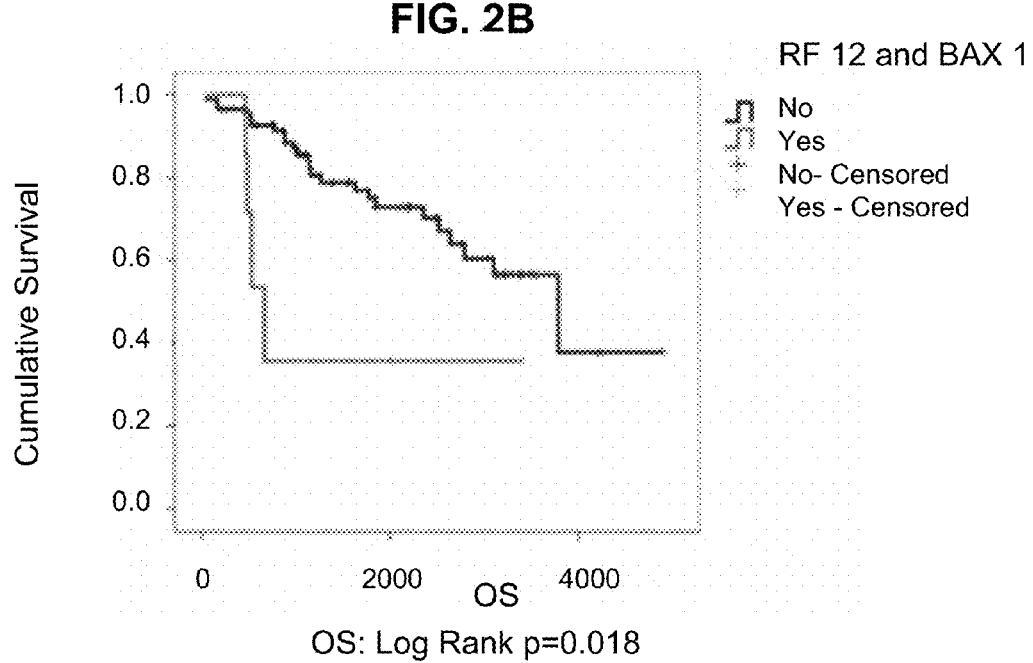

MATERIALS AND METHODS FOR PREDICTING RECURRENCE OF NON-SMALL CELL LUNG CANCER

CROSS-REFERENCE TO RELATED APPLICATIONS

This application claims priority to U.S. Provisional Patent Application No. 61/159,743, filed Mar. 12, 2009, the contents of which are hereby incorporated by reference in its entirety.

TECHNICAL FIELD

The present invention relates generally to the field of medical diagnostics. In particular, the present technology relates to methods of detecting genetic alterations associated with cancer.

BACKGROUND

Non-small cell lung cancer (NSCLC) is the dominant form of human lung cancer, representing almost 80% of the cancers in lung cancer patients. It usually grows and spreads more slowly than small cell lung cancer. There are three forms of NSCLC: adenocarcinomas are often found in an outer area of the lung; squamous cell carcinomas are usually found in the center of the lung by an air tube (bronchus), and large cell carcinomas can occur in any part of the lung. Large cell carcinomas tend to grow and spread faster than the other two types. Smoking causes most cases of lung cancer. Being around the smoke from others (secondhand smoke) also raises the risk for lung cancer. High levels of air pollution, working with or near cancer-causing chemicals or materials, and drinking water containing certain contaminants such as arsenic can increase the risk for lung cancer. Radiation therapy to the lungs can also increase the risk. Prognosis and selection of therapy for NSCLC are influenced by the stage of the cancer, the age of the patient, pathologic characteristics of the primary tumor, race and by general health. Three major treatments for cancer are surgery, radiation, and drug therapy. No treatment fits every patient, and often two or more treatments are required.

Various genes have been associated with an increased susceptibility to cancer. Evaluation of gene expression (e.g., stability of RNA and quantitation of expression) is refined and extended by measuring methylation profiles of CpG-containing sequences. Regions of unusually high GC content have been described in many genes and may be referred to as "CpG islands". The cytosine of CpG islands can be modified by methyltransferase to produce a methylated derivative: 5-methylcytosine (5me-C). If a methylated cytosine is located in the promoter region of a gene, the gene is likely to be silenced.

Tumor-specific changes in DNA methylation have been observed in many different malignancies and are frequently described as global hypomethylation combined with local hypermethylation. Global hypomethylation is linked to genomic instability of a tumor, whereas hypermethylation of specific genes correlates with their silencing and can induce point mutations owing to spontaneous deamination of 5me-C (transversion C>T). Silencing of a tumor suppressor gene can lead to enhanced transformation and increased tumor growth through disruption of the normal regulatory mechanisms of the affected cell.

SUMMARY

In one aspect, the present disclosure provides method for assessing NSCLC recurrence and survival in a subject, the method comprising detecting hypermethylation of the BAX promoter in a sample from the subject, wherein hypermethylation of the gene in the subject compared to a reference level is an indication of NSCLC recurrence or decreased 5-year survival. In one embodiment, the hypermethylation of the BAX promoter is detected by assessing the methylation state of at least one CpG region of the promoter. In some embodiments, the methylation of one or more positions −79, −58, or −51 of BAX promoter are detected.

In an illustrative embodiment, the methylation of position −79 of BAX promoter is detected. The methylation of position −79 of the BAX promoter may indicate a shorter time to recurrence (TTR) in the subject compared to when position −79 is not methylated. For example, methylation of position −79 of the BAX promoter may indicate a median TTR less than about 51 months.

In one embodiment, the methods further comprise detecting the methylation of position −53 of the RASSF1 promoter. The methylation of position −53 of the RASSF1 promoter and −79 of the BAX promoter may indicate a shorter TTR and shorter overall survival in the subject compared to when both positions are not methylated. For example, methylation of both position −53 of the RASSF1 promoter and −79 of the BAX promoter may indicate a median TTR less than about 10 months and a median overall survival of less than about 22 months. In one embodiment, the methods further comprise detecting methylation status of one or more of the genes selected from the group consisting of: p16, PTEN and DAPK.

In one embodiment, the detecting comprises converting the non-methylated cytosines present in the nucleic acids contained in the sample to uracils, amplifying the converted nucleic acids, and performing pyrosequencing on the amplified nucleic acids. In one embodiment, the detecting comprises converting the non-methylated cytosines present in the nucleic acids contained in the sample to uracils and performing methylation-specific PCR on the converted nucleic acids. In one embodiment, the detecting is assessed using an oligonucleotide that specifically hybridizes with the methylated form of the gene.

In one embodiment, the subject is a stage I-II NSCLC patient in which a tumor has been surgically resected. In one embodiment, the cells are obtained from a lung surgical or biopsy sample. In one embodiment, the cells are obtained from a bronchial lavage.

In one embodiment, the detecting hypermethylation is used in conjunction with other risk factors or indicators of NSCLC diagnosis or prognosis. In one embodiment, the risk factors or indicators are selected from the group consisting of: smoking history, family history, age, race, and histopathology.

In one aspect, the present disclosure provides a method for assessing NSCLC recurrence and survival in a subject, the method comprising detecting hypermethylation in a sample from the subject at one or more positions selected from the group consisting of: (a) position −1310 of the PTEN promoter; (b) position −53 of the RASSF1 promoter; (c) position −48 of the RASSF1 promoter; (d) position −1482 of the DAPK promoter; (e) position −79 of the BAX promoter; and (e) position −49 of the p16 promoter; wherein methylation of one or more positions in the subject compared to a reference level is an indication of NSCLC recurrence or survival.

In one embodiment, methylation of position −53 of the RASSF1 promoter, position −48 of the RASSF1 promoter, and/or position −1310 of the PTEN promoter indicates a shorter time to recurrence (TTR) in the subject compared to when position −53 of the RASSF1 promoter, position −48 of the RASSF1 promoter, and/or position −1310 of the PTEN promoter are not methylated. In one embodiment, methylation at position −53 of the RASSF1 promoter indicates a median TTR less than about 14 months. In one embodiment, methylation at position −48 of the RASSF1 promoter indicates a median TTR less than about 15 months. In one embodiment, methylation of position −1310 of the PTEN promoter indicates a median TTR less than about 27 months.

In another aspect, the present disclosure provides a method for assessing NSCLC recurrence and survival in a subject, the method comprising detecting hypermethylation in a sample from the subject at position −49 of the p16 promoter, wherein methylation at position −49 of the p16 promoter in the subject indicates a shorter TTR and shorter overall survival in the subject compared to when the position is not methylated, and wherein the subject is a patient first diagnosed with NSCLC at age 50 or younger.

Oligonucleotides or combinations of oligonucleotides that are useful as primers or probes in the methods are also provided. These oligonucleotides are typically provided as substantially purified material.

Kits comprising oligonucleotides which may be primers for performing amplifications as described herein are also provided. Kits may further include oligonucleotides that may be used as probes to detect amplified nucleic acid. Kits may also include restriction enzymes for digesting non-target nucleic acid to increase detection of target nucleic acid by oligonucleotide primers. In one aspect, the present disclosure provides, a kit for detecting hypermethylation associated with NSCLC recurrence and survival comprising at least one oligonucleotide selected from the group consisting of: SEQ ID NOs: 1-2, 4-21.

Other objects, features and advantages of the present invention will become apparent from the following detailed description. It should be understood, however, that the detailed description and the specific example, while indicating preferred embodiments of the invention, are given by way of illustration only, since various changes and modifications within the spirit and scope of the invention will become apparent to those skilled in the art from the detailed description.

DETAILED DESCRIPTION

Figure 1A:
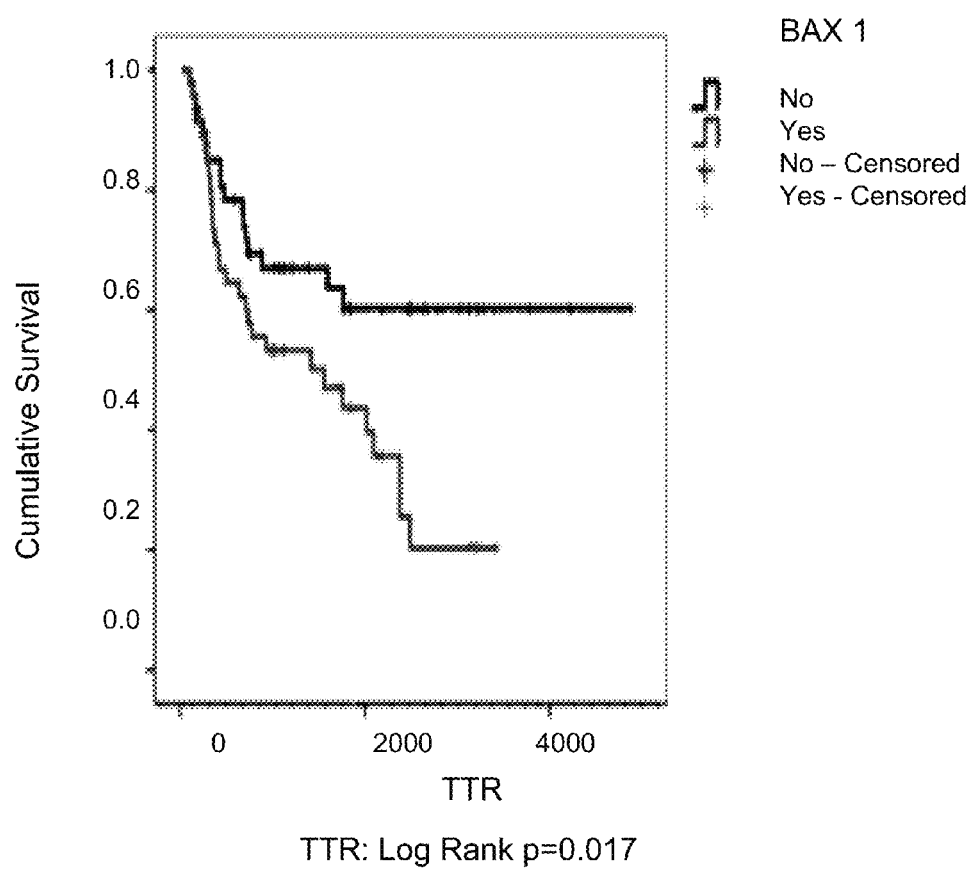
FIG. 1 is a chart showing time to recurrence (TTR) (FIG. 1A) and overall survival (OS) (FIG. 1B) with a cytosine in the BAX promoter at position −79 (the start of translation being +1) methylated or unmethylated.

In accordance with the present invention, methods are provided for detecting a nucleic acid segment of interest in a sample of nucleic acids. In particular embodiments, the nucleic acid segment of interest includes methylation markers that are informative for one or more of tumorigenesis, tumor progression, tumor aggressiveness, time to recurrence, and overall survival in non-small cell lung cancer (NSCLC).

In practicing the methods described herein, many conventional techniques in molecular biology, cell biology, and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *Oligonucleotide Synthesis*, Gait, Ed. (1984); *Transcription and Translation*, Hames & Higgins, Eds. (1984); Perbal, *A Practical Guide to Molecular Cloning*; the series, *Meth. Enzymol.*, (Academic Press, Inc., 1984); Buckingham and Flaws, *Molecular Diagnostics, Fundamentals, Methods and Clinical Applications*, (F. A. Davis Co., 2007)

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the terms "amplification" or "amplify" mean one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 2001, 29(11):E54-E54; Hafner et al., *Biotechniques* 2001, 30(4):852-6, 858, 860; Zhong et al., *Biotechniques*, 2001, 30(4):852-6, 858, 860.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein, the terms "diagnose" or "diagnosis" or "diagnosing" refer to distinguishing or identifying a disease, syndrome or condition or identifying a person having a particular disease, syndrome or condition. In illustrative embodiments of the invention, assays are used to diagnose a neoplastic disorder, such as NSCLC, in a subject based on an analysis of a sample.

As used herein, a "fragment" in the context of a nucleic acid refers to a sequence of nucleotide residues which hare at least about 5 nucleotides, at least about 7 nucleotides, at least about 9 nucleotides, at least about 11, nucleotides, or at least about 17, nucleotides. A fragment is typically less than about 300 nucleotides, less than about 100 nucleotides, less than about 75 nucleotides less than about 50 nucleotides, or less than about 30 nucleotides. In certain embodiments, the fragments can be used in polymerase chain reaction (PCR), or various hybridization procedures to identify or amplify identical or related DNA molecules.

As used herein, the terms "genomic nucleic acid" or "genomic DNA" refers to some or all of the DNA from a chromosome. Genomic DNA may be intact or fragmented (e.g., digested with restriction endonucleases). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*. John Wiley & Sons, Secaucus, N.J.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, the term "methylation profile" refers to a presentation of methylation status of one or more lung cancer disease marker genes in a subject's genomic DNA. In some embodiments, the methylation profile is compared to a standard methylation profile comprising a methylation profile from a known type of sample (e.g., samples known not to originate from a subject having a proliferative disease or samples known to originate from a subject having a specific proliferative disease such as lung cancer). In some embodiments, methylation profiles are generated using the methods of the present invention. The profile may be presented as a graphical representation (e.g., on paper or on a computer screen), a physical representation (e.g., a gel or array) or a digital representation stored in computer memory.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe.

An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "patient" refers to a subject who receives medical care, attention or treatment.

As used herein, the term "prognosis" refers to the prediction of the likelihood of cancer-attributable death or progression, including recurrence, metastatic spread, and drug resistance, of a neoplastic disease, such as NSCLC. The term "prediction" is used herein to refer to the likelihood that a patient will have a particular clinical outcome, whether positive or negative, following surgical removal of the primary tumor. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention and/or chemotherapy. The prediction may include prognostic factors.

As used herein, the term "positive clinical outcome" means an improvement in any measure of patient status, including those measures ordinarily used in the art, such as an increase in the duration of time to recurrence (TTR), an increase in the time of Overall Survival (OS), an increase in the time of Disease-Free Survival (DFS), and the like. An increase in the likelihood of positive clinical outcome corresponds to a decrease in the likelihood of cancer recurrence.

As used herein, the term monitoring disease "recurrence" in a subject refers to the monitoring of any aspect of disease progression or recurrence including, but not limited to, time to recurrence. In some embodiments, monitoring disease recurrence comprises determining the DNA methylation pattern of appropriate genes of the subject. As used herein, the term "time to recurrence" or "TTR" is used herein to refer to time in years to first NSCLC recurrence censoring for second primary cancer as a first event or death without evidence of recurrence.

As used herein, the term "overall survival" or "OS" is used to refer to time in years from surgery to death from any cause. The calculation of this measure may vary depending on the definition of events to be either censored or not considered.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human. In an exemplary embodiment, the sample is a tumor sample.

As used herein, "target nucleic acid" refers to segments of a chromosome, a complete gene with or without intergenic sequence, segments or portions a gene with or without intergenic sequence, or sequence of nucleic acids to which probes or primers are designed. Target nucleic acids may include wild type sequences, nucleic acid sequences containing mutations, deletions or duplications, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein, target nucleic acid may be native DNA or a PCR-amplified product. In one embodiment, the target nucleic acid is a fragment of a chromosome to be analyzed for methylation, e.g., a promoter region of a gene.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein the term "substantially identical" refers to a polypeptide or nucleic acid exhibiting at least 50%, 75%, 85%, 90%, 95%, or even 99% identity to a reference amino acid or nucleic acid sequence over the region of comparison. For polypeptides, the length of comparison sequences will generally be at least 20, 30, 40, or 50 amino acids or more, or the full length of the polypeptide. For nucleic acids, the length of comparison sequences will generally be at least 10, 15, 20, 25, 30, 40, 50, 75, or 100 nucleotides or more, or the full length of the nucleic acid.

Overview

Genetic and epigenetic events largely determine tumor phenotype and ultimately patient outcome. In carcinogenesis, tumor suppressor genes are frequently inactivated in two steps, starting with functional loss of one allele by a variety of mechanisms including mutations and methylation followed by deletion of the remaining allele. Methylation is the predominant mechanism for promoter inactivation by post-replicative epigenetic modification. Normally, stable or transient methylation at CpG dinucleotide promoter sequences coordinates gene expression during cell cycling. Aberrant methylation in tumor suppressor genes has been linked to disease course and outcome. Gene expression profiling in primary tumors and metastases have revealed molecular signatures associated with a metastatic phenotype.

In accordance with one aspect, the present invention relates to methods of detecting a methylation pattern in one or more genes associated with NSCLC. In some embodiments, the genes are selected from the group consisting of: BAX, BAD, BAK, BIK, BIM, RASSF1, RASSF5, PTEN, and DAPK. In some embodiments, the methylation pattern is detected in the promoter region of one or more of the BAX, BAD, BAK, BIK, BIM, RASSF1, RASSF5, PTEN, and DAPK genes. In some embodiments, the methylation of one or more of the BAX, BAD, BAK, BIK, BIM, RASSF1, RASSF5, PTEN, and DAPK genes is indicative of a shorter time to recurrence or lessened overall survival in a patient.

The present inventor has discovered that the BCL2-associated protein (BAX) DNA, in its methylated state, is a cancer-specific modification that can serve as a target for detection using assay methods. BAX is a central mediator of apoptosis. BAX and BAK, pro-apoptotic proteins containing homologous amino acid sequence domains along with related proteins such as BIM, counteract anti-apoptotic proteins such as BCL2 and BCL-XL to promote apoptosis. Activated BAX is involved in permeabilization of the mitochondrial outer membrane and release of mitochondrial factors that activate caspase proteins that execute the death program. Survival of abnormal cells is brought about, in part, by decreased expression of pro-apoptotic genes such as BAX and/or increased expression of activity of anti-apoptotic genes such as BCL2. BAX expression is controlled by the p53 transcription factor likely at a regulatory site upstream from the BAX protein coding region. It was previously unknown whether the addition of methyl groups to specific DNA sequences next to the BAX coding region would modify BAX expression.

In one embodiment, the assay examines a BAX methylation profile. In a second embodiment, the assay examines BAX methylation at a site −79 base pairs from the coding sequence for BAX in comparison to RASSF1 methylation at a site −53 base pairs from the coding sequence for RASSF1. In alternate embodiments, the test is examining a BAX methylation profile in comparison to the methylation profile for one or more of the following genes: BAD, BAK, BIK, BIM, RASSF1, RASSF5, PTEN or DAPK.

By targeting these specific genes and sites within these genes' promoters, the methods can be used to monitor patients and provide a prognosis for recovery after treatment for lung cancer. Treatment may be of any type known to those of skill in the art, including, but not limited to, surgical intervention, radiation therapy or chemotherapy using small molecules, biological molecules, etc., or a combination thereof. It is contemplated that testing for these methylation sites can be done before, during or after a treatment regimen or combination treatment and the resulting methylation analysis can be used to determine the continuation of a treatment or the addition of further treatments to reduce recurrence and increase overall survival.

In some embodiments, a biological sample is obtained from a subject (e.g., surgically removed tumor tissue, or tumor containing lymph nodes), which includes genomic DNA. The presence or absence of DNA methylation in the gene of interest and particularly in the CpG dinucleotide-rich region of the gene of interest generates a methylation profile for the subject. More specifically, the presence of 5-methylcytosine at positions −58 and −79 of the BAX promoter may be targeted. Methylation can be quantified by pyro sequencing of tumor tissue DNA from NSCLC patients.

A methylation profile refers to a presentation of methylation status of one or more marker genes in a subject's genomic DNA. In some embodiments, the methylation profile is compared to a standard methylation profile comprising a methylation profile from a known type of sample (e.g., cancerous or non-cancerous samples or samples from different stages of cancer). The profile may be presented as a graphical representation (e.g., on paper or on a computer screen), a physical representation (e.g., a gel or array) or a digital representation stored in computer memory.

One assay for detecting methylated nucleotides is based on treatment of genomic DNA with a chemical compound which converts non-methylated C, but not methylated C (i.e., 5 mC), to a different nucleotide base. One such compound is sodium bisulfite, which converts C, but not 5-mC, to U. Methods for bisulfite treatment of DNA are known in the art (Herman, et al., 1996, *Proc Nat'l Acad Sci* U.S. Pat. No. 93:9821-6; Herman and Baylin, 1998, *Current Protocols in Human Genetics*, N. E. A. Dracopoli, ed., John Wiley & Sons, 2:10.6.1-10.6.10). When DNA that contains unmethylated C nucleotides is treated with sodium bisulfite to give converted DNA, the sequence of that DNA is changed (C to U). Detection of U in the DNA is indicative of an unmethylated C.

The methods described herein are useful in conjunction with other methods for monitoring a recurrent versus a non-recurring lung cancer. For example, a methylation profile as described herein can be used by a diagnostician in conjunction with results from an image (e.g., MRI, X-Ray, etc.) of the lungs, results of tests run on lung tissue biopsies, and other tests used to monitor lung cancer in a patient. A cancer methylation profile is used to develop a prognosis for a recurrent lung cancer in a patient at an early stage wherein the aforementioned diagnostic tests would be used to determine an appropriate treatment regimen.

This patent application describes an efficient and unique panel of genes wherein the methylation analysis of one or a combination of the members of the panel enable the prognosis of lung cell proliferative disorders with a particularly high sensitivity, specificity and/or predictive value. Two key evaluative measures of any medical screening or diagnostic test are its sensitivity and specificity, which measure how well the test performs to accurately detect all affected individuals without exception, and without falsely including individuals who do not have the target disease (predictive value). Historically, many diagnostic tests have been criticized due to poor sensitivity and specificity.

Sample Collection and Preparation

The methods and compositions described herein may be used to detect nucleic acids associated with various genes using a biological sample obtained from an individual. The nucleic acid (DNA or RNA) may be isolated from the sample according to any methods well known to those of skill in the art. Biological samples may be obtained by standard procedures and may be used immediately or stored, under conditions appropriate for the type of biological sample, for later use.

Starting material for the detection assays is typically a clinical sample, which is suspected to contain the target nucleic acids. An example of a clinical sample is a tissue from a tumor. Next, the nucleic acids may be separated from proteins and sugars present in the original sample. Any purification methods known in the art may be used in the context of the present invention. Nucleic acid sequences in the sample can successfully be amplified using in vitro amplification, such as PCR. Typically, any compounds that may inhibit polymerases are removed from the nucleic acids.

Methods of obtaining test samples are well known to those of skill in the art and include, but are not limited to, aspirations, tissue sections, swabs, drawing of blood or other fluids, surgical or needle biopsies, and the like. The test sample may be obtained from an individual or patient. The test sample may contain cells, tissues or fluid obtained from a patient suspected being afflicted with or cancer, e.g., NSCLC. The test sample may be a cell-containing liquid or a tissue. Samples may include, but are not limited to, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the cells in the sample to detect using polymerase chain reaction.

Nucleic Acid Extraction

The nucleic acid to be amplified may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Buckingham and Flaws, *Molecular Diagnostics, Fundamentals, Methods & Clinical Applications*, F. A. Davis Co., pp. 65-70 (2007). Numerous commercial kits also yield suitable DNA and RNA including, but not limited to, QIAamp™ mini blood kit, Agencourt Genfind™, Roche Cobas® Roche MagNA Pure®, proteinase K or phenol:chloroform extraction using Eppendorf Phase Lock Gels®, and the NucliSens extraction kit (Biomerieux, Marcy l'Etoile, France).

In one aspect, the nucleic acids present in the sample are converted to modified nucleic acids prior to amplification. "Conversion" refers to the process whereby the non-methylated cytosines present in the nucleic acids are chemically deaminated and modified into uracils. Following amplification, thymidine residues are substituted for the deaminated cytosines. In some methods, the conversion is accomplished by contacting the nucleic acids with sodium bisulphite. Thus, in unmethylated DNA, this process results in all or mostly all cystosine (C) residues being replaced by thymidine (T), thereby converting a 4 base pair sequence into a 3 base pair sequence of A's, T's and G's. The bisulphite DNA conversion method for the detection of methylated DNA was described in Frommer et al., *PNAS* 89: 1827-1831 (1992) and Clark et al., *Nucl Acids Res* 22: 2990-7 (1994). Numerous commercial kits are available to perform the bisulfite conversion reaction including MethylEasy™ (Human Genetic Signatures), EpiTect® Bisulfite Kit (Qiagen/Epigenomics), and MethylAmp™ DNA Modification Kit (Epigentek).

Chemical conversion of cytosine to thymidine residues may be carried out as follows. First, the nucleic acid sample is denatured, if double stranded, to provide single-stranded nucleic acid. The denaturation step may be performed by contacting the nucleic acid with a NaOH solution, or other suitable alkaline reagent, or by heating. Second, the nucleic acid sample is reacted with a reagent and incubated so as to form a treated nucleic acid sample where any methylated nucleotides in the nucleic acid sample remain unchanged while unmethylated cytosine nucleotides are deaminated. Suitable reagents include, but are not limited to, sodium bisulfite. Third, the treated nucleic acid sample is purified to substantially remove any unwanted reagents or diluents from the treated nucleic acid sample. This may be accomplished, for example, by using column purification and concentration, or diluting the sample so as to reduce salt concentration and then precipitating the nucleic acid. A desulphonation step of the treated nucleic acid sample may be performed to remove sulphonate groups present on the treated nucleic acid so as to obtain a nucleic acid sample substantially free of sulphonate groups. Further detail regarding the conversion of non-methylated nucleotides can be found in U.S. Patent Application publications 20070020633, 20040219539, and 20040086944.

Non-methylated cytosine residues in both DNA strands are converted to uracil as a result of the process just described. Consequently, following conversion replication of the two strands will result in altered nucleic acid sequences.

Amplification of Nucleic Acids

Nucleic acid samples or isolated nucleic acids may be amplified by various methods known to the skilled artisan. Preferably, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase. When the template is sequence-modified, as described above, primers are designed so as to be complementary to the bisulfite-altered template. The amplification mixture preferably does not contain a UNG nuclease.

The primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended. An internal positive amplification control (IPC) can be included in the sample, utilizing oligonucleotide primers and/or probes.

Some methods employ methylation-specific PCR. Methylation-specific PCR (MSP) refers to a polymerase chain reaction in which amplification of the converted template sequence is performed. A set of primers, called methylation-specific primers, will amplify the converted template sequence if C bases in CpG dinucleotides within the target DNA are methylated. Primers for MSP are chosen such that the primers amplify the converted template sequence, which includes the target sequences, in an MSP reaction. The converted template sequence, and therefore the product of the MSP reaction, can be between 20 to 2000 nucleotides in length, preferably between 50 to 500 nucleotides in length, more preferably between 80 to 150 nucleotides in length. Typically, the methylation-specific primers result in an MSP product of a different length than the MSP product produced by the unmethylation-specific primers.

LCR is a method of DNA amplification similar to PCR, except that it uses four primers instead of two and uses the enzyme ligase to ligate or join two segments of DNA. LCR can be performed as according to Moore et al., *J Clin Micro*, 36(4):1028-1031 (1998). Briefly, an LCR reaction mixture contains two pair of primers, dNTP, DNA ligase and DNA polymerase representing about 90 μl, to which is added 100 μl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS*, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 min for the synthesis of RNA. The above steps are then repeated. Alternatively, after the initial cDNA synthesis, both RT and RNA polymerase are added following a 1 min 100° C. denaturation followed by an RNA elongation of approximately 30 min at 37° C. TAS can be also be performed on solid phase as according to Wylie et al., *J Clin Micro*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 μl TMA reaction mixture is placed in a tube, 200 μl oil reagent is added and amplification is accomplished by incubation at 42° C. in a water bath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *E. coli* Rnase H, and 32 U of T7 RNA polymerase. The amplification is carried out for 120 min at 41° C. in a total volume of 20 μl.

In a related method, self-sustained sequence-replication (3SR) reaction, isothermal amplification of target DNA or RNA sequences in vitro using three enzymatic activities:

reverse transcriptase, DNA-dependent RNA polymerase and *E. coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *Eur J Biochem*, 235:256-261, 1996).

SDA is an isothermal nucleic acid amplification method. A primer containing a restriction site is annealed to the template. Amplification primers are then annealed to 5' adjacent sequences and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo$^-$ Klenow polymerase). The sample mixture is heated 95° C. for 4 min to denature target DNA prior to addition of the enzymes. After addition of the two enzymes, amplification is carried out for 120 min at 37° C. in a total volume of 50 µl. Then, the reaction is terminated by heating for 2 min at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi, *Trends Biotechnol.*, 1991 9(2):53-8, 1991).

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity. Exemplary primers for detecting NSCLC-related genes are set forth in SEQ ID NOs: 1-2 and 4-21.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, *PCR Method Appl.*, 4:357-362; Tyagi et al, 1996, *Nature Biotechnology*, 14:303-308; Nazarenko et al., 1997, *Nucl. Acids Res.*, 25:2516-2521; U.S. Pat. Nos. 5,866,336 and 6,117,635).

Nucleic acids may be amplified prior to detection or may be detected directly during an amplification step (i.e., "real-time" methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

In one embodiment, detection of a target nucleic acid is performed using the TaqMan® assay, which is also known as the 5' nuclease assay (U.S. Pat. Nos. 5,210,015 and 5,538, 848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the target nucleic acids are useful in diagnostic assays for neoplastic disorders, such as NSCLC, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

Other methods of probe hybridization detected in real time can be used for detecting amplification of a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in some embodiments, amplified fractions are separated on an agarose gel and stained with ethidium bromide by methods known in the art to detect amplified fragments.

As a quality control measure, an internal amplification control may be included in one or more samples to be extracted and amplified. The skilled artisan will understand that any detectable sequence that is not typically present in the sample can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Kits

The test can be produced as a kit for characterizing recurrent versus a nonrecurring lung cancer and includes reagents for (e.g., sufficient for) detecting the presence or absence of DNA methylation in one or more genes. Instructions for using the kit for characterizing recurrent lung cancer in the subject are included and the instructions required by the United States Food and Drug Administration for use in in vitro diagnostic products. The reagents include reagents for amplification of gene-specific DNA fragments.

EXAMPLES

The present invention is further illustrated by the following examples, which should not be construed as limiting in any way.

Example 1

Characterization of BAX Gene Methylation in NSCLC Patients

The BAX protein induces cell death by counteracting the BCL2 oncogene protein. Promoter methylation of the tumor suppressor gene, RASSF1, which indirectly down-regulates BCL2 expression, has been associated with shorter survival in Stage I and II NSCLC. In this example, the epigenetic regulation, particularly methylation of the BAX 5' region, was examined.

Subject Population.

The patient demographics are shown in Table 1. The median time to recurrence (TTR) was 69.1 mos and median overall survival was 125 mos for this group of patients selected to have equal representation of recurrent (47) and non-recurrent (49) cases within five years.

TABLE 1

Patient Demographics

| Characteristic | No. patients | (%) |
|---|---|---|
| Total | 96 | 100 |
| Age | | |
| <60 years | 28 | 29.2 |
| >60 years | 68 | 70.8 |
| Gender | | |
| Male | 42 | 42.8 |
| Female | 54 | 56.3 |
| Ethnicity | | |
| Caucasian | 71 | 75.5 |
| African American | 22 | 23.4 |
| Unknown | 1 | 1.1 |
| Smoking status | | |
| Yes | 65 | 67.7 |
| Never smoked | 17 | 17.7 |
| Unknown | 14 | 14.6 |
| Histopathological subtype | | |
| Adenocarcinoma | 51 | 53.1 |
| Squamous Cell Carcinoma | 33 | 34.4 |
| Other | 12 | 12.5 |
| Stage | | |
| 1b | 62 | 64.8 |
| 2a | 8 | 8.3 |
| 2b | 26 | 27.1 |

DNA Isolation:

DNA was extracted by digestion of tumor and normal cells manually scraped from 0.2 to 1 cm regions of thin sections of paraffin-embedded tissue samples in a solution of 50 microliters of Lysis Mix (50 mM KCl; 10 mM Tris, pH 7.8; 2 mM MgCl$_2$; 20 mM DTT; 1.7 µM SDS; 0.5 µg/µl proteinase K). DNA from white blood cells was isolated by inorganic extraction according to manufacturer's recommendations (Qiagen, Inc., Valencia Calif.).

Methylation Analysis:

Bisulfite treatment of DNA was performed using the Qiagen Epitech (Qiagen Inc., Valencia, Calif.) system. Twenty microliters (20 µl) of DNA lysate was mixed with bisulfite solution and DNA protect buffer and subjected to the following program: 99° C., 5 min; 60° C., 25 min; 99° C., 5 min; 60° C., 85 min; 99° C., 5 min; 60° C., 175 min; and 20° C. hold. The converted DNA was cleaned with silica columns supplied with the Epitect kit and eluted in 40 µl of Epitect elution buffer, according to manufacturer's directions.

The converted DNA was amplified with primers to the BAX promoter region. There primers were specially designed to recognize the bisulfite treated DNA: Forward primer 5' GGTATTTATY GGGAGATGTT TATTGGATAG 3' (SEQ ID NO: 1); Reverse primer 5'-(biotin) TCACCCCCGC CTCTAAACTA CTCC-3' (SEQ ID NO: 2). The PCR amplification program was: 95° C., 15 min; 94° C., 30 sec; 52° C., 1 min; 72° C., 30 sec; 72° C., 10 min; 4° C. hold. The resulting PCR products comprise a region from −215 to +38 of the BAX gene (A of ATG is +1), as set forth in SEQ ID NO: 3 below:

```
ATCGGGAGAT GCTCATTGGA CAGTCACGTG ACGGGACCAA

ACCTCCCGAG GGAGCGAGGC AGGTGCGGTC ACGTGACCCG

GCGGCGCTGC GGGGCAGCGG CCATTTTGCG GGGCGGCCAC

GTGAAGGACG CACGTTCAGC GGGGCTCTCA CGTGACCCGG

GCGCGCTGCG GCCGCCCGCG CGGACCCGGC GAGAGGCGGC

GGCGGGAGCG GCGGTGATGG ACGGGTCCGG GGAGCAGCCC

AGAGGCGGGG GTGA
```

The bisulfite treatment converts unmethylated cytosines to uracil, but not methylated cytosines, therefore, the PCR products will contain thymine bases replacing the unmethylated cytosines.

Pyrosequencing Assay:

The biotinylated PCR products were incubated with streptavidin-conjugated Sepharose beads in a 96 well plate format. The double-stranded amplicons now attached to the beads were captured with a vacuum device (part of the Pyro-Mark MD system), denatured and washed so that only the reverse strands remained. The reverse strand is the template for sequencing with the PyroMark MD luminometer. The results from the pyrosequencing procedure were expressed as percent methylation at each potentially methylated cytosine in the sequenced region that is the percent of the templates in the well that read as C vs. T. The overall average percent of the promoter is the average of the percent methylation levels at the individual sites.

Statistical Analysis:

All statistics were performed on SPSS (Statistical Package for the Social Sciences) software. Methylation levels at individual sites were compared to patient demographics using the independent samples Methylation data was dichotomized with a cutpoint of <2% (unmethylated) and >2% (methylated), although other cutpoints could be used. Alternative qualitative methods may also be used which provide data as methylated/unmethylated without numerical value. Time to recurrence and survival in methylated and unmethylated groups were analyzed using the Kaplan Meier test.

Results:

The CpG dinucleotide-rich region of BAX displayed tumor-specific hypermethylation in 31 of 96 cases (32.3%; Table 2).

TABLE 2

Percent of Stage I and II cases methylated[a].

|  | BAX |
|---|---|
| Methylated[b] | 31 |
| Unmethylated | 65 |
| Percent | 32.3 |

[a]Overall promoter methylation
[b]Methylation status determined as levels more than 7%

Table 3 shows overall average methylation in the BAX promoter compared to patient demographics Overall average promoter methylation was 5.48+2.76% in NSCLC compared to 3.53+0.99% in non-malignant lung tissue. Methylation of CpG at position −58 of the BAX promoter was greater in males than in females (p=0.046).

TABLE 3

Overall average promoter methylation levels and patient characteristics*

|  | BAX |
|---|---|
| Overall | 5.43 |
| Age |  |
| <60 years | 5.00 |
| ≥60 years | 5.56 |
| Gender |  |
| Female | 5.10 |
| Male | 5.85 |
| Ethnicity |  |
| Caucasian | 5.51 |
| African American | 5.43 |
| Smoking |  |
| No | 4.53 |
| Yes | 5.55 |
| Histopathology |  |
| Adenocarcinoma | 5.48 |
| SCC | 5.31 |
| Stage |  |
| 1B | 5.40 |
| 2a, 2b | 5.52 |

*Average methylation levels of all CpGs analyzed in the BAX promoter. Methylation of BAX CpG at −79 was higher in smokers than in non-smokers (p = 0.015; Table 4).

TABLE 4

Methylation levels at specific BAX CpG sites

|  | BAX |
|---|---|
| Age | NS[a] |
| Gender |  |
| Female | 8.25 |
| Male | 11.42 |
| Site | −58 |
| p value | 0.046 |
| Ethnicity | NS |
| Smoking |  |
| No | 1.67 |
| Yes | 3.51 |
| Site | −79 |
| p value | 0.015 |
| Histopathology |  |
| Adenocarcinoma | 11.2 |
| SCC | 18.9 |
| Site | −51 |
| p value | 0.103 |
| Stage | NS |

[a]NS - no sites were significant

Figure 1B:
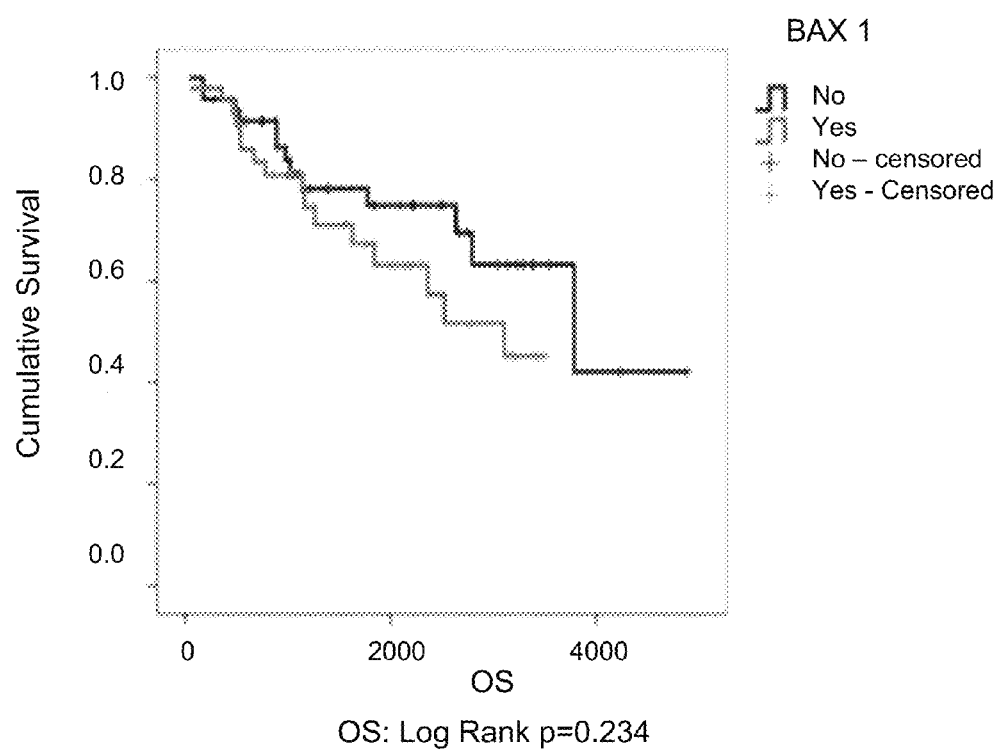
Figure 2A:
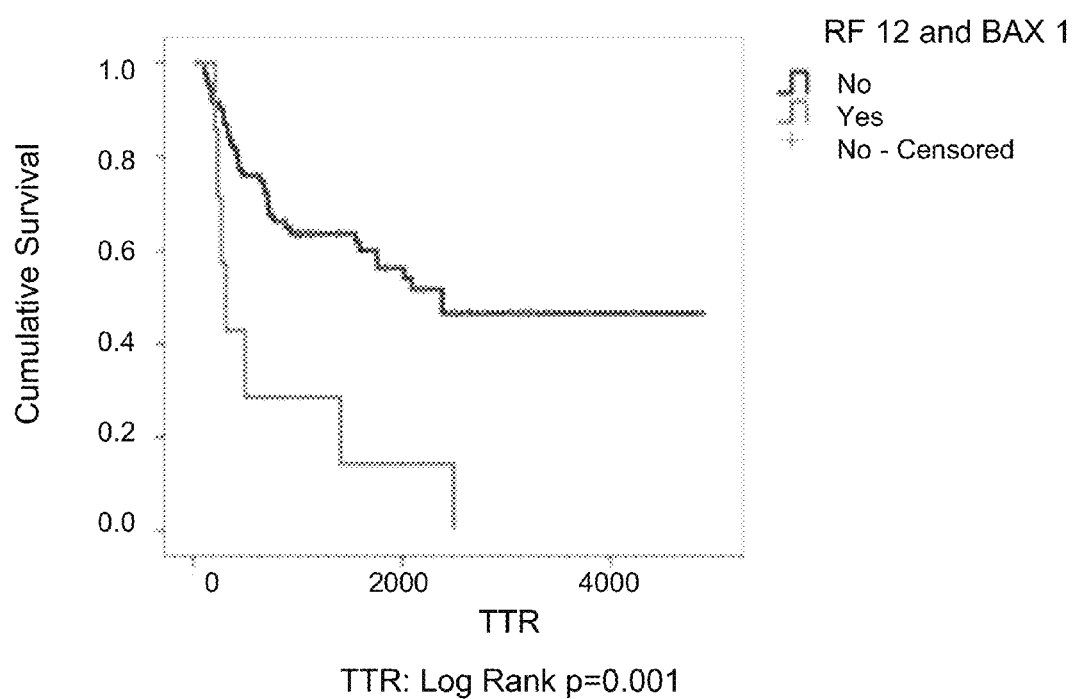
FIG. 2 is a chart showing TTR (FIG. 2A) and OS (FIG. 2B) with BAX at position −79 and RASSF1 at position −53 methylated or unmethylated.

Hypermethylation of BAX CpG at −79 was associated with shorter TTR (p=0.017), but not OS (FIG. 1). When BAX −79 and RASSF1 −53 sites were both hypermethylated, TTR was significantly shorter (10.3 mos, 95% 016.50 to 14.2 mos vs median not reached; p=0.001) as was OS (22.1 mos vs 125 mos; p-0.018; FIG. 2). Recurrence within five years (10.3 mos, 95% C16.5 to 14.1 mos vs median not reached; p=0.006) and five-year survival (22.1 mos, 95% CI 11.2 to 33.0 mos vs median not reached; p=0.005) were also significantly lower than when either or neither gene promoter was hypermethylated (Table 5).

TABLE 5

CpG site methylation, recurrence and survival.

| Gene (site) | n | Cutpoint % | Median (months) | p |
|---|---|---|---|---|
| Recurrence | | | | |
| BAX | 47 | ≥2 | 51.4 | |
| | 46 | <2 | (NR)[a] | 0.017 |
| BAX(−79) + RASSF1 (−53) | 47 | >2 and ≥30 | 10.3 | |
| | 46 | <2 or <30 | (NR)[a] | 0.001 |
| Overall Survival | | | | |
| BAX (−79) | 15 | ≥2 | 102 | |
| | 73 | <2 | 125 | 0.234 |
| BAX (−79) + RASSF1 (−53) | 7 | >2 or >30 | 22.1 | |
| | 85 | <2 or <30 | 125 | 0.018 |

[a](NR) = median not reached

These data demonstrate tumor-specific methylation of the 5' region of the BAX gene in lung cancer, and more specifically, at certain sites in the promoter region (e.g., 79 base pairs from the start of the BAX protein coding region). The data also demonstrate tumor-specific methylation of the 5' region of the RASSF1 gene in lung cancer, and more specifically at certain sites in the promoter region (e.g., 53 base pairs from the start of the RASSF1 protein coding region). These sites represent target biomarkers for determining recurrence and overall survival for patients that have been treated for lung cancer. The effect of BAX 5' methylation on TTR and OS is synergistic with methylation of RASSF1 in this patient group.

Example 2

PTEN, RASSF1, and DAPK Site Specific Hypermethylation and Outcome in NSCLC Patients For this study, promoter methylation of genes involved in a variety of cellular functions including adhesion (CDH1), DNA repair (MGMT), gene expression (LET7), cell division (p16, RASSF1, RASSF5) and survival (DAPK, PTEN), was compared with time to recurrence and survival in surgically treated early stage lung cancer patients.

Patients and Clinical Assessment.

Tumor material used in this study was from Stage Ia, Ib, IIa and IIb surgically treated NSCLC patients. Analysis was first performed on tumors from a training group of 75 patients (35 adenocarcinoma, 26 squamous cell carcinoma, 14 other) and then an independent validation group of 57 patients (28 adenocarcinoma, 23 squamous cell carcinoma and 6 other). Reference DNA from 22 normal leukocyte samples and 20 nonmalignant lung specimens was also tested. For all 132 NSCLC patients and 20 nonmalignant lung samples, fixed tumor specimens were obtained from the Department of Pathology, Rush University Medical Center (Chicago, Ill.). Diagnosis of NSCLC was acquired from pathology reports and histologic evaluation. Clinical data were established from chart review. Follow-up included radiographic imaging with histological verification of recurrence. Time to recurrence (TTR) and overall survival (OS) were measured in months from the date of diagnosis to the time of disease progression or death. Recurrent cases included any recurrence. Seventy nine percent of recurrences were less than 40 months after surgery. Eighty two percent of deaths from lung cancer occurred in less than 60 months. Equal numbers of nonrecurrent cases were selected for this study, with follow-up from 1 to 12 years after surgery. All cases were staged according to the TNM classification criteria (6th edition). This study was approved by the Rush University Medical Center Institutional Review Board with waiver of individual consent.

Immunohistochemistry.

Immunohistochemistry (IHC) specimens were 5.0 µm sections of formalin-fixed paraffin-embedded tumor tissue or sections from cytology cell blocks. Immunostaining methods and reagents were according to standard procedures. Staining frequency and intensity of all tumor cells on each slide were estimated on scales of 0 to 4 without knowledge of clinical patient data. Intensity was judged from background and relative density of staining. For frequency, less than 1% positive tumor cells per field was scored as 0, 1-10% as 1, 11-35% as 2, 36-70% as 3, and over 70% as 4. IHC expression was dichotomized into 2 levels: positive (intensity×frequency>4) and negative (intensity×frequency≤4).

Fluorescence In Situ Hybridization.

For fluorescent in situ hybridization (FISH), specimen slides were hybridized with two-color FISH probe solutions (PTEN/CEP7 LSI) in a HYBrite™ automated codenaturation oven (Abbott Diagnostics, Downers Grove, Ill.). DAPI stain was applied to the specimen for visualization of the nuclei. PTEN/CEP7 ratios <0.75 were interpreted as PTEN loss.

Methylation Analysis.

DNA was extracted by proteinase K digestion of tumor and normal cells manually microdissected from paraffin-embedded tissue samples. DNA from white blood cells was isolated by inorganic extraction (Qiagen, Inc., Valencia Calif.). Bisulfite treatment of DNA was performed using the Qiagen Epitech system according to manufacturer's protocol. This system is designed to minimize adduct-induced strand breakage during and after conversion. Following bisulfite treatment, the converted DNA was amplified using primers designed for the altered sequences (Biotage, Inc., Uppsala, Sweden; EpigenDx, Worcester, Mass.). PCR was performed with HotStarTaq (Qiagen) according to the manufacturer's protocol using modified primers (Table 6). Amplicons were resolved by agarose electrophoresis to confirm proper amplification and quality of product.

TABLE 6

Primer sequences

| Primer | Sequences | SEQ ID NO: |
|---|---|---|
| CDH1 Forward | ATTTTAGTAATTTTAGGTTAGAGGGTTA | SEQ ID NO: 4 |
| CDH1 Reverse | biotin-ACCACAACCAATCAACAAC | SEQ ID NO: 5 |
| CDH1 Sequencing | ATGGTTATTTTTGTTTAGATGAG | SEQ ID NO: 6 |
| DAPK Forward | GAGGGTAGTTTAGTAATGTGTTATAGG | SEQ ID NO: 7 |
| DAPK Reverse | biotin-CCTCCCAACTACCCTACCAAA | SEQ ID NO: 8 |

TABLE 6-continued

Primer sequences

| Primer | Sequences | SEQ ID NO: |
|---|---|---|
| DAPK Sequencing | ATGGTTATTTTTGTTTAGATGAG | SEQ ID NO: 9 |
| LET7 Forward | ATGGTTATTTTTGTTTAGATGAG | SEQ ID NO: 10 |
| LET7 Reverse | biotin-ACCCTAAAAATAAAAACATTATAA | SEQ ID NO: 11 |
| LET7 Sequencing | ATGGTTATTTTTGTTTAGATGAG | SEQ ID NO: 12 |
| PTEN Forward | GGATGTGGGTGTTTGTGTAATTA | SEQ ID NO: 13 |
| PTEN Reverse | biotin-CAATAATAACCCCTCACCCTTAA | SEQ ID NO: 14 |
| PTEN Sequencing | TTTGTGTAATTAGTTTTTTA | SEQ ID NO: 15 |
| RASSF1 Forward | AGTTTGGATTTTGGGGGAGG | SEQ ID NO: 16 |
| RASSF1 Reverse | biotin-CAACTCAATAAACTCAAACTCCCC | SEQ ID NO: 17 |
| RASSF1 Sequencing | GGGTTAGTTTTGTGGTTT | SEQ ID NO: 18 |
| RASSF5 Forward | GGAATTTTGTAGTTGTTTTAGGTGAA | SEQ ID NO: 19 |
| RASSF5 Reverse | biotin-TTTAAAAAAACCCCAACCTACTAAAC | SEQ ID NO: 20 |
| RASSF5 Sequencing | AAGAAGTTTTTAAATTTATATT | SEQ ID NO: 21 |
| p16, MGMT | PyroMark ™ (Biotage) | |

The detection of the C/T polymorphisms that result from PCR amplification of bisulfite-treated DNA was performed by Pyrosequencing™ (Biotage) on a PyroMark MD pyrosequencer. Luminescent signal generated from the incorporation of nucleotides complementary to the test template is normalized and quantified. For each C/T polymorphism, the relative percent C (methylated) vs. T (unmethylated) at that position is reported. Non-CpG cytosines, which should be 100% converted, are included in each sequence to confirm complete conversion. This method was used to detect and quantify the degree of methylation for each CpG within each sample promoter being investigated. The following previously reported regions (CpG islands) of hypermethylation were analyzed (A of ATG of the start of translation=+1): CDH1, −160 to −121; p16, −64 to −40; LET7, −158 to −116; RASSF1, −57 to −36; RASSF5, −224 to −177; DAPK, −1518 to −1406; MGMT, −37 to −19; PTEN, −1333 to −1276. The output data includes site-specific percent methylation for each CpG in the analyzed area as well as overall average percent methylation, which is the average of the CpG levels within the promoter.

TABLE 7

Sequences studied for methylation.

| Gene | Sequence analyzed[1] | SEQ ID NO: |
|---|---|---|
| CDH1 | YGYGTTTATGYGAGGTYGGGTGGGYGGGTYGTTAGTTTYG | SEQ ID NO: 22 |
| DAPK | GGGGYGTTYGYGTTTYGGGYGGAYGTATTGGTTTTTYGGTYGGYG | SEQ ID NO: 23 |
| LET7 | YGGTAYGTTYGTGAAGTYGTTATTTAGTTAGTTTGGGGGTTAYGAG | SEQ ID NO: 24 |
| MGMT | YGTTTTGYGTTTYGAYGTTYGYAGG | SEQ ID NO: 25 |
| RASSF5 | YGYGTAGAYGTYGTTTGGTAYGGATTTTATTTTTTTYGGTTYGTYGGYGGTTTTTTTGGGTYGTTTTTTTTGTTATTTYGATTTTTTT | SEQ ID NO: 26 |
| P16 | GGGTGGGGYGGATYGYGTGYGTTYGGYGGTTGYGGA | SEQ ID NO: 27 |
| PTEN | AGYGTTAGTTTYGATAGYGTTTTTTYGGGAGGTTGGTTYGAGT | SEQ ID NO: 28 |
| RASSF1 | YGTTYGGTTYGYGTTTGTTAGYGTTTAAAGTTA | SEQ ID NO: 29 |

[1]Y are potential sites of methylation

Statistical Analysis.

The associations between percent methylation and binary covariates were tabulated, and Fisher's exact test was used to measure their significance. For purposes of survival analysis, percent methylation levels at each CpG site, were divided into two classes (yes/no) using site-specific cutpoints. These cutpoints were chosen based on the results from the training data and the same cutpoints used for the validation group. The Kaplan-Meier method was used to estimate the probability of recurrence and the probability of survival as functions of time. Survival differences among comparator groups were analyzed by the log-rank test. Predictors that were statistically significant or marginally significant in univariate analyzes or were deemed to be clinically or biologically important were included as candidate covariates in multivariate Cox proportional hazards (PH) regression models. Statistical analyzes were done using Version 9.1.3 of the SAS software (SAS Institute), SPSS version 15 and the statistical software R. All reported p-values are two sided. P-values between (0.05-0.10), (0.01-0.05) and (<0.01) are respectively reported as marginally significant, significant and strongly significant.

Patient characteristics. Table 8 shows patient characteristics and clinical status for the training and validation groups. Median ages in these two groups were 62.8 and 65.2 years, respectively. In the combined group, 91 of 132 tumors (68.9%) were more than 3 cm in diameter. Lobectomies accounted for 106/131 (80.9%) surgeries. Other surgical types included 10 (7.6%) segmentectomies, 12 (9.2%) pneumonectomies and 3 (2.3%) sleeve lobectomies. The median Median OS for the combined training and validation groups was significantly shorter for patients who received adjuvant chemotherapy than for those who did not (p=0.011). OS, but not TTR, was significantly shorter in males than for females (p=0.039). Patients with tumor size more than 3 cm at diagnosis had significantly shorter OS (p=0.049). We did not find any other significant association of patient characteristics with either TTR or OS in either patient group. Recurrent and nonrecurrent cases did not differ with regard to age, gender, ethnicity, stage or smoking status. Recurrent cases were significantly more likely to have received chemotherapy (p=0.000 and p=0.003 in the training and validation groups, respectively).

Overall Average Promoter Methylation.

Methylation was measured quantitatively. Percent methylation varied from gene to gene. The methylation state was dichotomized using gene-specific cutpoints to define hypermethylation. These cutpoints for overall average promoter methylation were selected based on average measurements for each gene in the training data; the same cutpoints (10-50%) were used for the validation and combined data. Table 2 shows the number of cases in the training and validation groups where hypermethylation (percent methylation more than the gene-specific cutpoint) was observed for the genes tested. Frequently hypermethylated (percent methylation above the gene-specific cutpoint) promoters included the PTEN promoter, which was methylated in 49.2% of the cases (training and validation groups combined), the RASSF5 promoter (34.4% of cases) and RASSF1 (37.5% of cases). As has been observed in other studies, the LET7 promoter was heavily methylated, with more than 50% methylation in 99% of cases.

TABLE 8

Patient Demographics

| Characteristic | Training Group | | Validation Group | |
|---|---|---|---|---|
| | Number of Patients | % | Number of Patients | % |
| Total | 75 | 100 | 57 | 100 |
| Age | | | | |
| <60 years | 24 | 32.0 | 18 | 31.6 |
| >60 years | 51 | 68.0 | 39 | 68.4 |
| Gender | | | | |
| Male | 32 | 42.7 | 27 | 47.4 |
| Female | 43 | 7.3 | 30 | 52.6 |
| Ethnicity | | | | |
| Caucasian | 54 | 74.0 | 43 | 75.4 |
| African American | 17 | 23.3 | 13 | 22.8 |
| Unknown | 2 | 2.7 | 1 | 1.8 |
| Smoking Status | | | | |
| Yes | 46 | 61.3 | 44 | 77.2 |
| Never Smoked | 10 | 13.3 | 7 | 12.3 |
| Unknown | 19 | 25.3 | 6 | 10.5 |
| Adjuvant Chemotherapy | | | | |
| Yes | 29 | 38.7 | 16 | 28.1 |
| No | 45 | 60.0 | 40 | 70.2 |
| Unknown | 1 | 1.3 | 1 | 1.8 |
| Histopathological Subtype | | | | |
| Adencarcinoma | 35 | 46.7 | 28 | 49.1 |
| Squamous Cell Carcinoma | 26 | 34.7 | 23 | 40.4 |
| Other | 14 | 18.7 | 6 | 10.5 |
| Stage | | | | |
| 1b | 42 | 56.0 | 39 | 68.4 |
| 2a | 8 | 10.7 | 3 | 5.3 |
| 2b | 25 | 33.3 | 15 | 26.3 |
| Recurrence | | | | |
| Yes | 46 | 61.3 | 21 | 36.8 |
| No | 29 | 38.7 | 36 | 63.2 |

TABLE 9

Percent of Stage I and II Cases Methylated

| | P16 | MGMT | DAPK | RASSF1 | RASSF5 | PTEN | LET | CDH1 |
|---|---|---|---|---|---|---|---|---|
| Training | | | | | | | | |
| Hypermethylated[1] | 11 | 8 | 16 | 22 | 18 | 37 | 27 | 21 |
| Not hypermethylated | 59 | 57 | 50 | 42 | 45 | 30 | 0 | 53 |
| Percent | 15.7 | 10.6 | 24.2 | 34.3 | 28.1 | 55.2 | 100 | 28.4 |

TABLE 9-continued

Percent of Stage I and II Cases Methylated

|  | P16 | MGMT | DAPK | RASSF1 | RASSF5 | PTEN | LET | CDH1 |
|---|---|---|---|---|---|---|---|---|
| Validation |  |  |  |  |  |  |  |  |
| Hypermethylated[2] | 15 | 6 | 5 | 23 | 15 | 22 | 50 | 11 |
| Not hypermethylated | 40 | 54 | 47 | 32 | 14 | 31 | 1 | 39 |
| Percent | 27.2 | 11.1 | 9.6 | 41.1 | 48.2 | 41.5 | 98 | 22.0 |

[1]Gene-specific methylation status determined as levels more than 10 average methylation levels for each gene for all samples in the training group.

We did not find significant association of overall average promoter methylation levels with age over 60, gender, ethnicity, adjuvant chemotherapy and stage. Average promoter methylation of p16 was higher in squamous cell carcinoma pathology than in adenocarcinoma (Table 10); the difference was significant ($p=0.04$) in the training group, not significant in the smaller validation group, but was significant ($p=0.02$) when the two groups are combined. On the other hand, promoter methylation of MGMT was marginally higher in smokers than in nonsmokers in the training group ($p=0.058$), but significantly higher in the validation group ($p=0.024$) and combined groups ($p=0.006$). Overall average promoter methylation levels of RASSF1 was significantly different between smokers and nonsmokers in combined groups ($p=0.029$), but not in either of the component groups.

overall promoter methylation levels averaged 3.86% in leukocytes, 12.2% in nonmalignant lung and 17.1% in NSCLC cases. All three of the nonmalignant lung specimens with elevated RASSF1 promoter methylation levels were from smokers. This is consistent with observations of lower levels of the RASSF1 transcripts found in bronchial epithelia from smokers. LET7 promoter methylation levels over 50% were present in both leukocytes and nonmalignant lung. LET7 overall average percent promoter methylation levels were 62.0% in leukocytes, 67.5% in nonmalignant lung and 70.4% in NSCLC cases. The overall average and individual CpG promoter methylation levels are provided in the accompanying Supplement.

TABLE 10

Overall average promoter methylation levels and demographic groups

|  | P16 | MGMT | DAPK | RASSF1 | RASSF5 | PTEN | LET | CDH1 |
|---|---|---|---|---|---|---|---|---|
| Smoking |  |  |  |  |  |  |  |  |
| Training |  |  |  |  |  |  |  |  |
| No | 5.56 | 6.90[1] | 7.56 | 14.252[2] | 10.14 | 12.67 | 72.0 | 13.30 |
| Yes | 10.36 | 10.98 | 9.24 | 16.98 | 9.46 | 11.38 | 70.2 | 14.17 |
| Validation |  |  |  |  |  |  |  |  |
| No | 7.29 | 3.43[1] | 4.14 | 9.43[2] | 13.33 | 17.20 | 61.1 | 8.50 |
| Yes | 8.38 | 6.76 | 5.23 | 15.14 | 10.61 | 12.36 | 72.0 | 11.79 |
| Adjuvant Chemotherapy |  |  |  |  |  |  |  |  |
| No | 9.31 | 8.12 | 7.71 | 15.16 | 10.33 | 10.19 | 68.5 | 12.94 |
| Yes | 8.53 | 8.81 | 7.55 | 19.49 | 11.90 | 11.93 | 72.3 | 12.46 |
| Histopathology |  |  |  |  |  |  |  |  |
| Training |  |  |  |  |  |  |  |  |
| Adenocarcinoma | 6.94[3] | 10.11 | 9.07 | 17.86 | 10.29 | 12.72 | 74.8 | 13.79 |
| SCC | 16.35 | 11.88 | 8.87 | 15.84 | 9.18 | 10.48 | 70.3 | 14.04 |
| Validation |  |  |  |  |  |  |  |  |
| Adenocarcinoma | 7.04[3] | 7.52 | 5.42 | 16.18 | 14.00 | 10.07 | 70.8 | 10.85 |
| SCC | 10.00 | 6.14 | 6.43 | 12.95 | 11.00 | 10.59 | 74.7 | 12.00 |

[1]Training; p = 0.058; validation: p = 0.024; combined p = 0.006.
[2]Training: p = 0.649; validation: p = 0.163; combined p = 0.02; 0.041; validation: p = 0.159; combined p = 0.020.

Methylation Levels Compared to Normal Tissue.

Qualitatively, methylation levels in normal blood cells and nonmalignant lung were low in 6 of the genes tested showing that elevated methylation levels (>10-15%, depending on the gene) observed in these genes was cancer-specific. Two genes, RASSF1 and LET7 had increased overall promoter methylation levels in normal tissues. Increased methylation was observed in 3 of 17 RASSF1 nonmalignant lung specimens compared to 0 of 21 normal blood samples. RASSF1

Methylation Levels at Individual CpG Sites Along Each Promoter.

The site-specific percent methylation of each of multiple CpG cytosines within each promoter was measured. In general, consistent patterns of methylation levels were observed across the promoters for each gene, that is, methylation levels were relatively higher or lower at particular sites within the same promoter for the majority of patients. Graphs of percent methylation vs. promoter site for NSCLC, nonmalignant lung and leukocytes are shown in Supporting information.

Site-Specific Methylation Levels Vs. Demographics.

Among patient characteristics, smoking history was found to be strongly associated with altered tumor methylation status involving cytosine at position −35 of the MGMT gene (p=0.002, 0.024 and 0.001 in the training, validation and combined groups respectively) and cytosine at position −1507 of the DAPK gene (p=0.008, 0.033 and <0.001 in the training, validation and combined groups respectively) (Table 11). Methylation levels of DAPK at position −1486 were lower in stage Ib than in stage II (p=0.005 and 0.063 in the training and validation groups, respectively). Methylation levels in a separate group of stage Ia patients was 4.71% (data not shown). Methylation of p16 at cytosine site −46 was significantly lower in adenocarcinoma than in squamous cell carcinoma in the training and combined groups (p=0.034 and 0.009).

Methylation at Individual CpG Sites, Time to Recurrence and Survival.

The association of site-specific hypermethylation (at individual CpG sites) with TTR is evaluated using the Kaplan-Meier method and log-rank test. Results are shown in Table 12 and FIG. 3. Site-specific cutpoints, selected based on percent methylations levels showing significant effects in the training data, were used to define the site-specific hypermethylated state for each cytosine within each gene promoter. Site-specific hypermethylations at five specific CpG sites in four genes, RASSF1, PTEN, RASSF5 and DAPK, were found to be significantly associated with TTR in the training group (Table 12). The directions of association were the same in all five CpG sites; site-specific hypermethylations were associated with shorter survival in all five sites.

TABLE 11

Methylation Levels at Specific Promoter Sites

| | Gene | Training | Validation | Gene | Training | Validation |
|---|---|---|---|---|---|---|
| Smoking | MGMT[1] | | | DAPK[2] | | |
| No | | 5.40 | 3.29 | | 3.89 | 3.14 |
| Yes | | 11.22 | 6.62 | | 11.10 | 5.95 |
| Site | −35 | | | −1507 | | |
| p value | | 0.002 | 0.024 | — | 0.008 | 0.033 |
| Histopathology | P16[3] | | | | | |
| Adenocarcinoma | | 4.46 | 7.04 | | | |
| SCC | | 14.72 | 9.50 | | | |
| site | −46 | | | | | |
| p value | | 0.034 | 0.234 | | | |
| Stage | DAPK[4] | | | | | |
| 1b | | 17.51 | 9.30 | | | |
| 2a, 2b | | 32.85 | 16.13 | | | |
| site | | | | | | |
| p value | | 0.005 | 0.063 | | | |

[1]Combined training and validation p = 0.0001.
[2]Combined training and validation p < 0.001.
[3]Combined training and validation p = 0.009.
[4]Combined training and validation p = 0.001.

TABLE 12

CpG site Hypermethylation and Time to Recurrence

| | Training Group | | | Validation Group | | |
|---|---|---|---|---|---|---|
| Gene (site) | n | Median (months) | p | n | Median (months) | Combined[1] p |
| DAPK (−1486) | | | | | | |
| Y | 40 | 25.5 | | 17 | (NR)[2] | |
| N | 21 | 112 | 0.019 | 35 | (NR) | 0.557 |
| DAPK (−1482) | | | | | | |
| Y | 15 | 10.0 | | 7 | 54.8 | |
| N | 47 | 66.7 | 0.012 | 45 | (NR) | 0.547 |
| RASSF1 (−53) | | | | | | |
| Y | 16 | 13.7 | | 9 | 13.9 | |
| N | 48 | 64.0 | 0.038 | 47 | (NR) | 0.087 |
| RASSF1 (−48) | | | | | | |
| Y | 17 | 14.4 | | 9 | 13.9 | |
| N | 47 | 64.0 | 0.030 | 47 | (NR) | 0.087 |
| RASSF5 (−188) | | | | | | |
| Y | 39 | 25.5 | | 23 | 54.8 | |
| N | 23 | 112 | 0.014 | 1 | (NR) | 0.299 |
| PTEN (−1310) | | | | | | |
| Y | 11 | 26.9 | | 3 | 13.5 | |
| N | 53 | 69.1 | 0.012 | 48 | (NR) | 0.134 |

[1]TTR p values for training and validation groups combined.
[2](NR) = median not reached.

Validation of Methylation at Individual CpG Sites, Time to Recurrence and Survival.

In the validation group, hypermethylation in the two sites in RASSF1 were marginally associated with TTR. Although the associations with TTR were not significant in the other three genes in the validation group, promoter hypermethylation at the indicated sites was always found with shorter TTR. When the training and validation groups are combined, all 5 CpG sites are significantly associated (three out of the five are strongly) with TTR. The directions of association were again identical at all five sites with hypermethylation being associated with shorter TTR.

Figure 3:
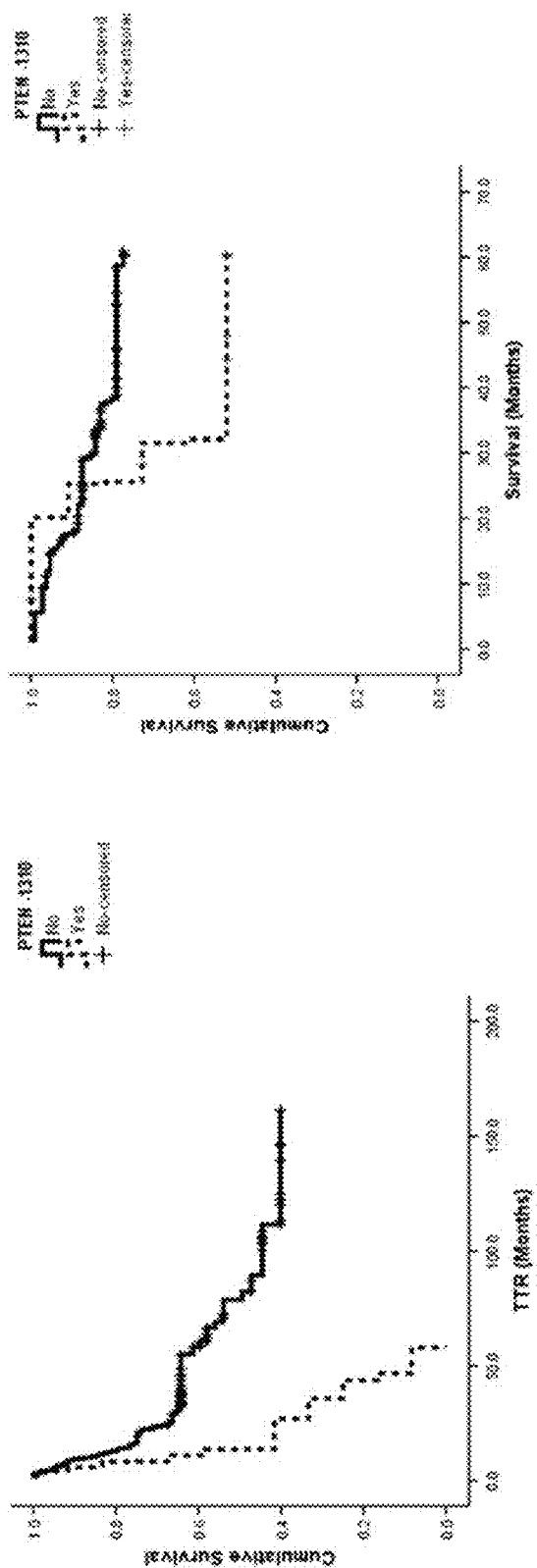
FIG. 3 is a series of charts showing Kaplan-Meyer curves for recurrence (left) and five-year survival (right) for combined training and validation groups. On left, survival curves are shown for site-specific hypermethylation of PTEN site −1310, RASSF1 site −53, MGMT site −35 and p16 site −64 vs. recurrence: Log rank p<0.000, p=0.004, p=0.387 and p=0.695, respectively. On right, site-specific hypermethylation of PTEN site −1310, RASSF1 site −53, MGMT site −35 and p16 site −46 vs. 5 year survival: Log rank p=0.078, p=0.002, p=0.003 and p=0.131, respectively.
Figure 3:
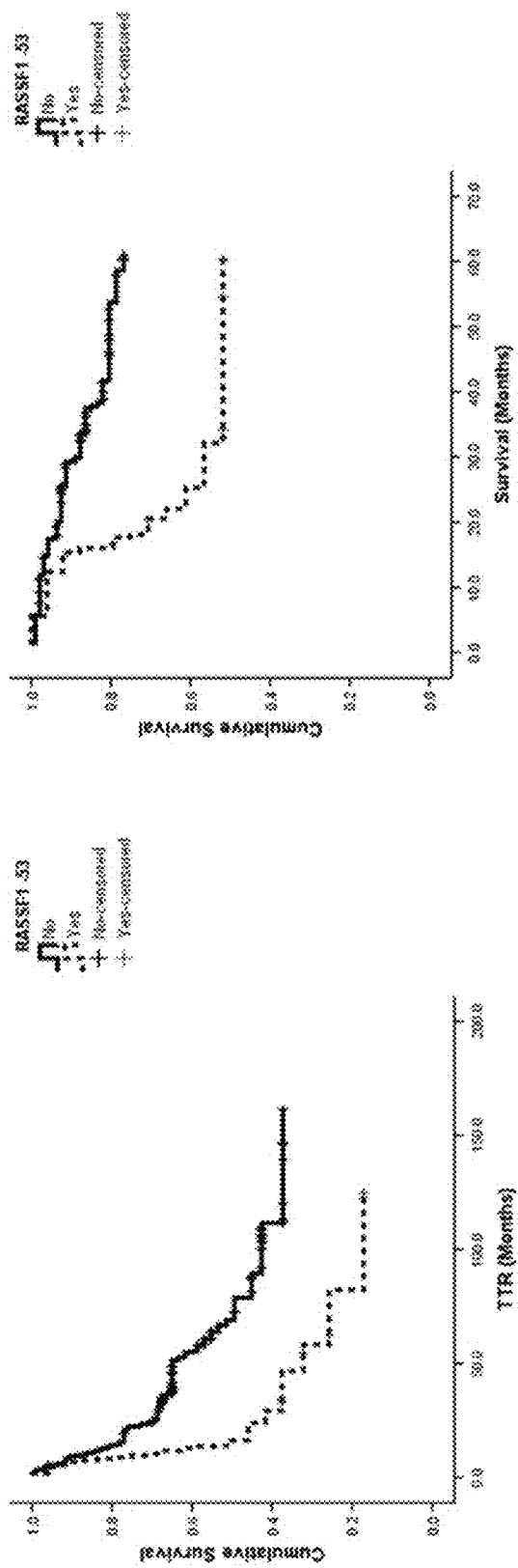
Figure 3:
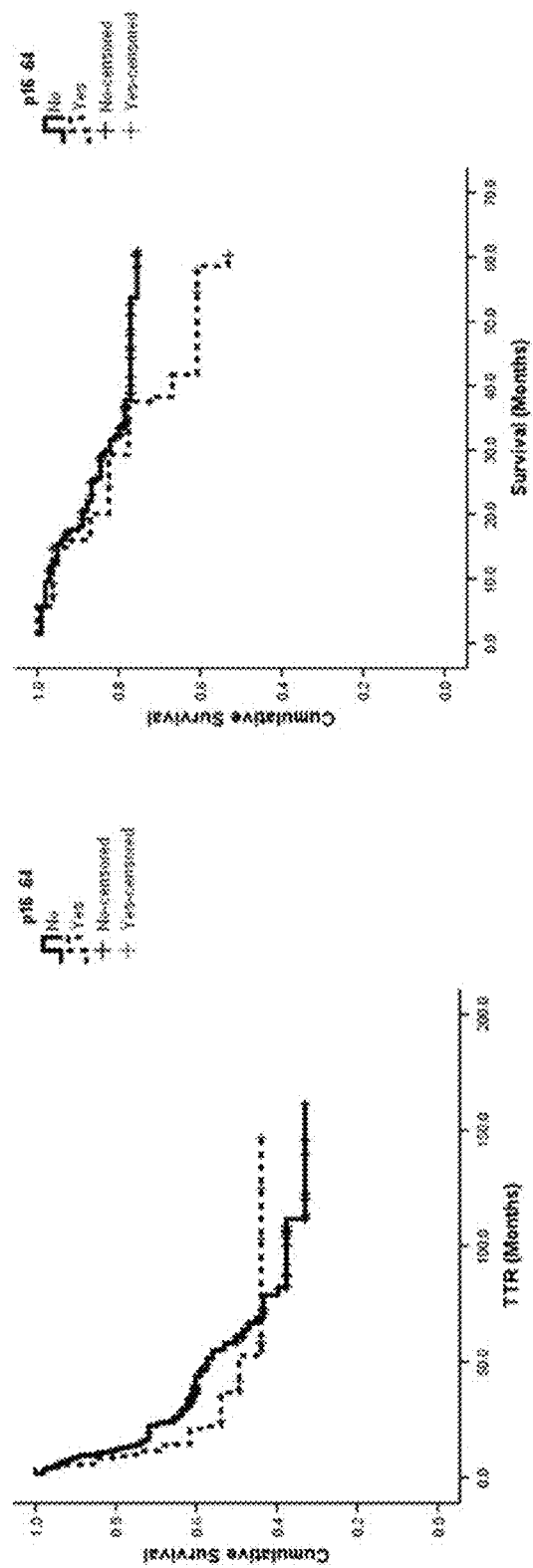

Table 12 shows p values for the separate and combined training and validation groups. The marginal significance in the validation group for RASSF1 and PTEN led to a more highly significant association when the groups were combined. Methylation of site −1310 in the PTEN promoter >23% was associated with shorter TTR than methylation less than 23% (13.5 mos, 95% CI 9.04 to 18.0 vs. 82.3 months, 95% CI 39.7 to 125; p<0.001; FIG. 3). Hypermethylation (methylation ≥30%) of site −53 in the RASSF1 promoter was significantly associated with shorter TTR (16.3 mos, 95% CI 0.00 to 33.0) than methylation <30%, (78.8 mos, 95% CI 34.6 to 123; p=0.002). A similar correlation was seen at an adjacent CpG site −48 (p=0.003).

With regard to survival, hypermethylation (methylation ≥30%) of RASSF1 at position −53 was also significantly associated with shorter survival than with methylation <30% (median survival 32.1 mos vs. median not reached; p=0.017). Hypermethylation (methylation ≥30%) of RASSF1 at position −53 was also significantly associated with shorter survival than with methylation <30% (p=0.002). Hypermethylation of the MGMT (methylation ≥18%) promoter site −35 was correlated with shorter survival (p=0.003), as was hypermethylation (methylation ≥11%) of p16 at site −49 (p=0.010; FIG. 3).

PTEN Methylation, Deletion and Protein Expression.

Figure 4A:
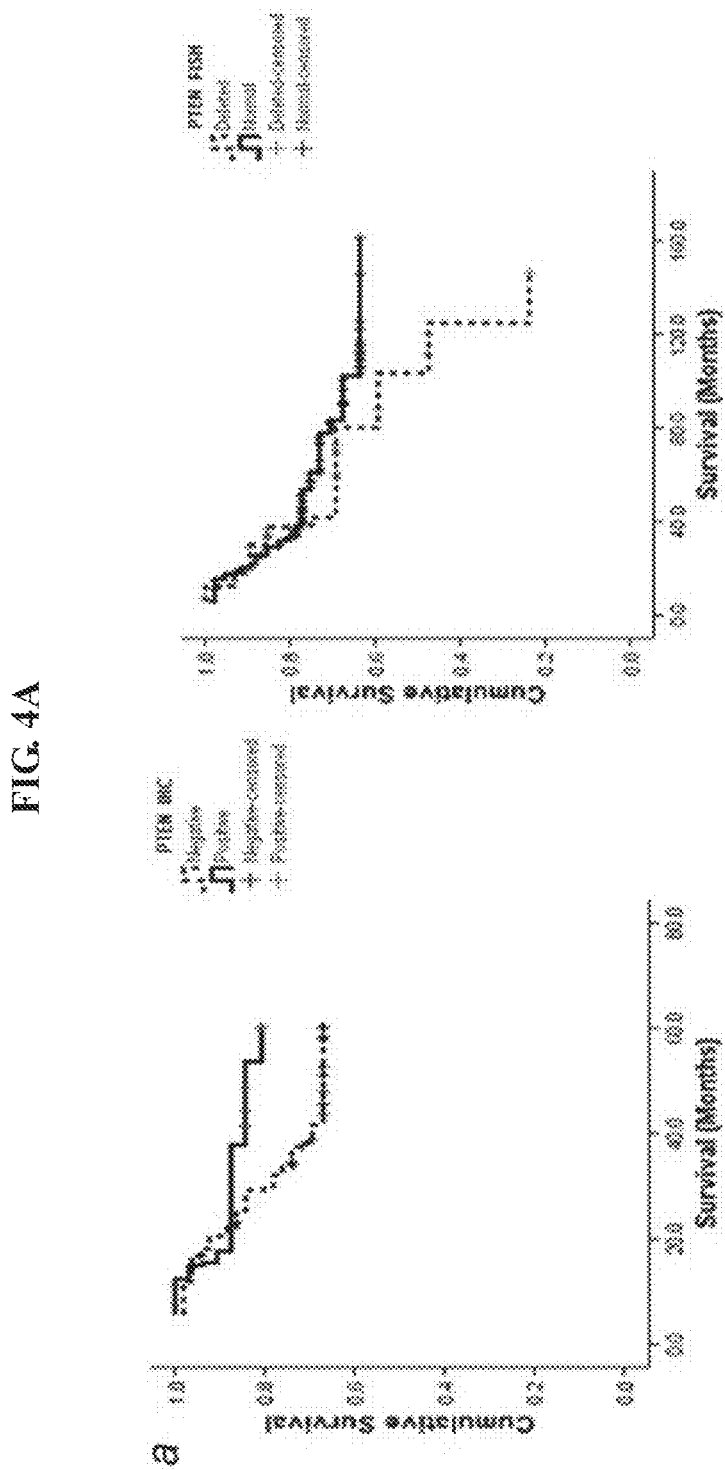
FIG. 4A is a chart showing Kaplan-Meyer survival curves for deletion status of PTEN protein expression (left) and PTEN loss (right) vs. survival. Log rank p=0.186 for protein expression and p=0.439 for deletion.

In previous studies, PTEN protein expression was associated with longer survival in late stage lung cancer patients treated with Iressa. In the current study, PTEN promoter hypermethylation showed a correlation with shorter TTR in early stage patients. PTEN protein expression and genomic status were analyzed by immunohistochemistry and fluorescence in situ hybridization (FISH), respectively. Although no marker was significantly associated with survival, the results are consistent with deletion, hypermethylation or low PTEN protein expression having an adverse effect on survival (FIG. 4A).

Figure 4B:
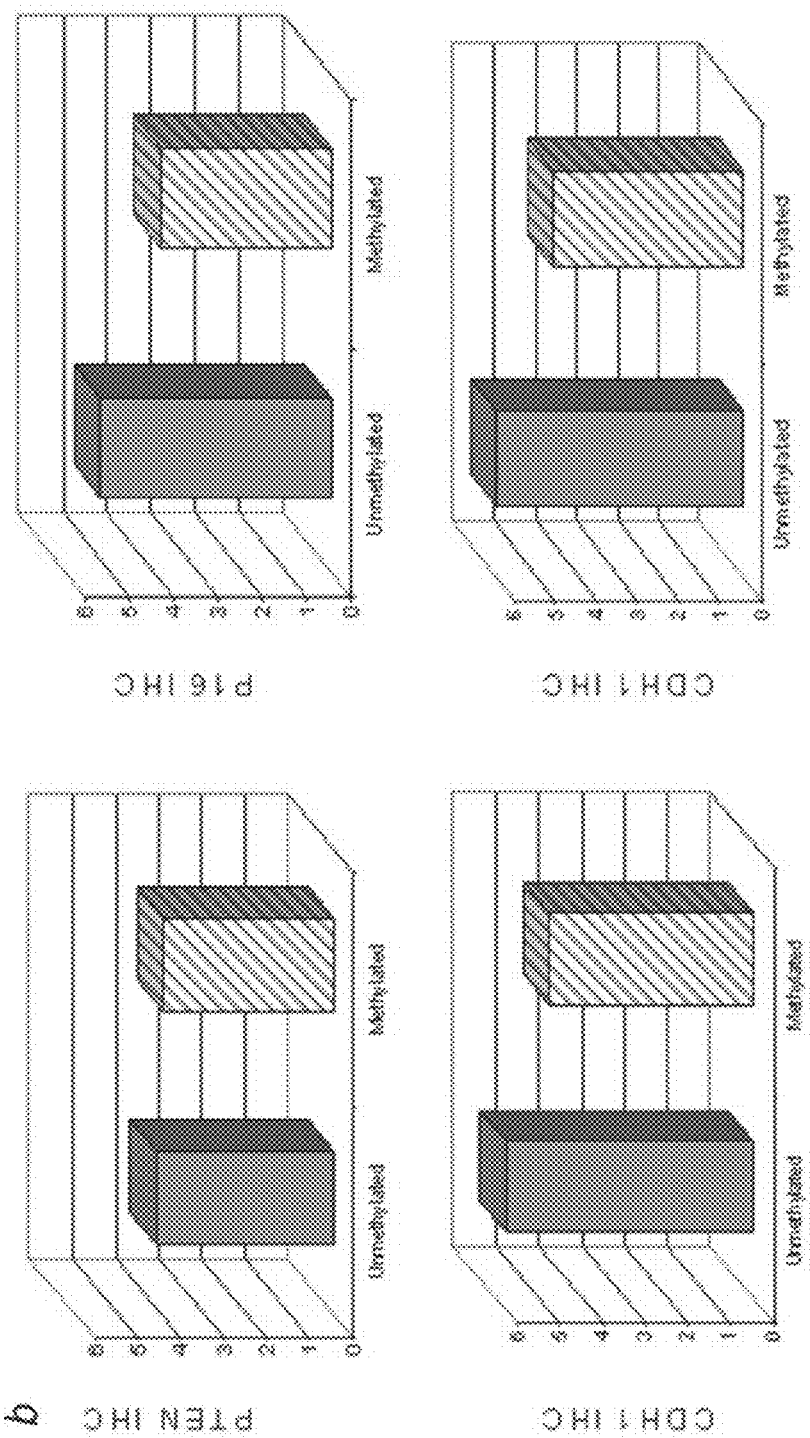
FIG. 4B shows protein expression levels of PTEN (top left), p16 (top right) and CDH1 (bottom left) vs. hypermethylation state at positions −1310, +148 and −150, respectively. Hypermethylation of LET7 at −153 resulted in higher expression of CDH1 protein (bottom right).

Protein expression was slightly lower with hypermethylation of PTEN at −1310. Similar results were observed for CDH1 and p16 protein expression. It has been reported that LET7 microRNA down-regulates CDH1. Methylation of the LET7 promoter at −116>67% resulted in higher levels of CDH1 protein (frequency×intensity=6.38) than methylation ≤67% (frequency×intensity=5.33; FIG. 4B).

Multivariate Analysis.

Multivariate Cox PH regression was used to estimate the effect of demographic, immunohistochemical and epigenetic study variables on TTR in the combined training and validation groups. Baseline variables such as age at diagnosis, smoking status, ethnicity, histology, stage and methylation status of CpG sites that were significantly associated with TTR in univariate analyses (Table 12), were included in the multivariate model. Variable selection methods were used to reduce the number of predictors and to arrive at the final model DAPK hypermethylated at −1486 had the smallest adjusted p-value for predicting recurrence in this multivariate model (p<0.001, HR 1.93, CI 1.06 to 3.53) followed by PTEN at −1310 (p=0.001, hazard ratio 3.63, 95% CI 1.61 to 8.17, n=132).

A similar strategy was followed for multivariate Cox PH regression analysis of five year survival. Male gender (p=0.01, HR=3.36, 95% CI 1.34 to 8.43), CDH1 hypermethylation at −143 (p=0.018, HR=5.07, 95% CI 1.32 to 19.40) and RASSF1 hypermethylation at −48 (p=0.040, HR=2.71, 95% CI 1.05 to 7.0) were also significantly associated with shorter survival.

This study reveals a possible relationship between promoter hypermethylation of phosphatidyl inositol 3 kinase inhibitor PTEN, and ras associated protein RASSF1 at specific cytosine residues and shorter TTR and five year survival in two small stage I and II NSCLC patient groups. Furthermore, hypermethylation of a specific promoter cytosine in the death-associated kinase gene, DAPK was associated with shorter TTR in these patient groups. Several studies have been designed to investigate the clinical significance of epigenetic state of selected genes and gene sets in lung cancer. Many methylation studies on lung and other cancers make use of methods that qualitatively analyze particular sites within the gene promoter. This study was performed using a method that quantifies methylation levels at multiple CpG sites within each gene promoter, affording a more detailed survey of the methylation state.

Quantification of methylation by this approach revealed consistent patterns of CpG methylation levels across gene promoters. The patterns observed for the p16 and CDH1 promoter CpG methylation levels were similar to patterns previously reported for these promoters. Different CpG sites within the same promoter may show no methylation or high or variable levels of methylation. Studies based on single methylation sites, therefore, may be inconsistent, depending on which sites are being analyzed. Furthermore, the degree of methylation of each CpG site can vary, with respect to actual biological effect. Methylation status predictive of outcome may, therefore, be revealed by testing different levels of methylation at multiple CpG sites.

Two of the 8 tumor suppressor genes tested had significantly higher methylation of at least one promoter CpG site in smokers, compared to nonsmokers. The strongest correlations with smoking were with DAPK at cytosine position −1507 (combined training and validation groups p<0.001) and MGMT at position −35 (combined training and validation groups p=0.001). In addition, overall average promoter methylation of RASSF1 was higher in smokers than in nonsmokers (combined training and validation groups p=0.029). Weakened DNA repair capability (for example by loss of MGMT function) has been connected to better response to nitrosourea compounds in some cancers. Loss of apoptotic functions, however, would compromise cell death induced by unrepaired DNA damage. Cells with increased DNA repair (lower promoter methylation of MGMT) and decreased apoptosis (higher promoter methylation of DAPK or RASSF1) might be more resistant to therapeutic intervention.

Comparison of methylation of multiple CpG sites in the p16 promoter vs. histopathology revealed that methylation of p16 at position −46 was higher in squamous cell carcinoma than in adenocarcinoma (combined training and validation groups p=0.020). Association of promoter hypermethylation of p16 but not RASSF1, RASSF5 nor MGMT with histopathology is consistent with observations made by Blanco et al., supporting an inflammation-induced lung adenocarcinoma model.

Brock et al. observed an association between recurrence in stage Ia patients and promoter hypermethylation of p16 at one of the sites (−64) investigated in this study. We did not observe significantly longer TTR with hypermethylation at −64 nor −59 in the stage Ib, IIa and IIb training and validation groups, however, we did observe an association between hypermethylation of p16 CpG site −64 and shortened survival time in a separate group of stage Ia patients (n=54; p=0.046; data not shown). Results reported by Brock et al., unlike ours, did not show significant associations between RASSF1 hypermethylation and recurrence. RASSF1 hypermethylation at −48 was related to shortened survival even in out stage Ia group, further supporting results seen in the later stage training and validation groups (data not shown).

Global gene expression profiling studies have identified multigene signatures associated with outcome. Since different criteria are used for data analysis, no consistent gene panels nor biological pathways have been identified. The correlation between recurrence and survival and hypermethylation of specific RASSF1, DAPK or PTEN CpG sites in this study suggests that hypermethylation of one or a few genes may be prognostic.

Example 3

Age-Related Promoter Methylation and Outcome in Surgically-Treated Stage I-II NSCLC Patients To explore apoptotic and epigenetic influences, promoter methylation (silencing) at multiple CpG dinucleotides of selected tumor suppressor genes, including BCL2 associated X protein (BAX) was analyzed in stage I and II NSCLC patients. Methylation was quantified at specific CpG sites in p16, MGMT, BAX, DAPK, RASSF1, CDH1, LET7-3-a, NORE1(RASSF 5), and PTEN promoters in assessable tumor tissue from 196 surgically treated NSCLC patients by pyrosequencing. Molecular and clinical characteristics with time to recurrence (TTR) and overall survival (OS) were evaluated.

Four of five genes with promoter methylation levels associated with age were related to apoptosis. Methylation levels of specific promoter sites in BAX, DAPK, PTEN, p16 and RASSF5 were significantly higher in patients with age at diagnosis over 40 years than in those patients with diagnosis at 40 years or younger in this patient group. Methylation levels at −79 in the BAX promoter (A of ATG=+1) were significantly higher in the >40 group than in the ≤40 group ($p<0.001$). The results were less significant using a cutoff of 50 years or younger ($p=0.024$). In Kaplan-Meier analysis, patients with age at diagnosis ≤40 had shorter median OS than those over 40 (18.3 mos vs 114 mos, Log rank $p=0.018$). Patients with age at diagnosis ≤40 also had shorter median TTR than those over 40 (18.3 mos vs 114 mos, Log rank $p=0.018$). When p16 was hypermethylated at cytosine position −49, patients with diagnosis ≤50 years had shorter TTR (9.9 mos vs 78.8 mos; $p=0.098$). and significantly shortened OS (14.9 mos vs 125 mos; $p=0.008$). No such effect was seen in patients >50. Promoter methylation of PTEN resulted in significantly shortened TTR regardless of age. No age-related effect (>40 to >60 years) on recurrence and survival was seen with BAX nor DAPK promoter methylation.

BAX promoter methylation at −79 was significantly lower, and not associated with outcome in patients ≤40 years. Overall, these data support an influence of hypermethylation in the p16 promoter (proliferation), but not BAX, DAPK nor PTEN (apoptosis) and outcome specifically in young patients after surgical resection for stage I and II NSCLC.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for assessing non-small cell lung cancer (NSCLC) recurrence and survival in a subject, the method comprising detecting hypermethylation of the Bcl-2-associated X protein (BAX) promoter in a sample of NSCLC tissue from the subject, wherein the methylation of position −79 of BAX promoter is detected, and further wherein hypermethylation of the gene in the subject compared to a reference level is an indication of NSCLC recurrence or decreased 5-year survival.

2. The method of claim 1, wherein methylation of position −79 of the BAX promoter indicates a shorter time to recurrence (TTR) in the subject compared to when position −79 is not methylated.

3. The method of claim 2, wherein methylation of position −79 of the BAX promoter indicates a median TTR less than about 51 months.

4. A method for assessing non-small cell lung cancer (NSCLC) recurrence and survival in a subject, the method comprising detecting hypermethylation of the Bcl-2-associated X protein (BAX) promoter in a sample of NSCLC tissue from the subject, wherein the methylation of position-53 of the Ras association domain-containing protein 1 (RASSF1) promoter is detected.

5. The method of claim 4, wherein methylation of position −53 of the RASSF1 promoter and −79 of the BAX promoter indicates a shorter TTR and shorter overall survival in the subject compared to when both positions are not methylated.

6. The method of claim 5, wherein methylation of both position −53 of the RASSF1 promoter and −79 of the BAX promoter indicates a median TTR less than about 10 months and a median overall survival of less than about 22 months.

7. The method of claim 1 further comprising detecting methylation status of one or more of the genes selected from the group consisting of: cyclin-dependent kinase inhibitor 2A (p16), phosphatase and tensin homolog (PTEN) and death-associated protein kinase (DAPK).

8. The method of claim 1, wherein the subject is a stage I-II NSCLC patient in which a tumor has been surgically resected.

9. The method of claim 1, wherein the detecting comprises converting the non-methylated cytosines present in the nucleic acids contained in the sample to uracils, amplifying the converted nucleic acids, and performing pyrosequencing on the amplified nucleic acids.

10. The method of claim 1, wherein the detecting comprises converting the non-methylated cytosines present in the nucleic acids contained in the sample to uracils and performing methylation-specific PCR on the converted nucleic acids.

11. The method of claim 1, wherein the cells are obtained from a lung surgical or biopsy sample.

12. The method of claim 1, wherein the cells are obtained from a bronchial lavage.

13. A method for assessing non-small cell lung cancer (NSCLC) recurrence and survival in a subject, the method comprising detecting hypermethylation of the Bcl-2-associated X protein (BAX) promoter in a sample from the subject, wherein the methylation of position −79 of BAX promoter is detected, and further detecting hypermethylation in a sample from the subject at one or more positions selected from the group consisting of:
   (a) position −1310 of the phosphatase and tensin homolog (PTEN) promoter;
   (b) position −53 of the Ras association domain-containing protein 1 (RASSF1) promoter;
   (c) position −48 of the RASSF1 promoter; and
   (d) position −1482 of the death-associated protein kinase (DAPK) promoter;
   wherein methylation of one or more positions in the subject compared to a reference level is an indication of NSCLC recurrence or survival.

14. The method of claim 13, wherein methylation of position −53 of the RASSF1 promoter, position −48 of the RASSF1 promoter, and/or position −1310 of the PTEN promoter indicates a shorter time to recurrence (TTR) in the subject compared to when position −53 of the RASSF1 promoter, position −48 of the RASSF1 promoter, and/or position −1310 of the PTEN promoter are not methylated.

15. The method of claim 13, wherein methylation at position −53 of the RASSF1 promoter indicates a median TTR less than about 14 months.

16. The method of claim 13, wherein methylation at position −48 of the RASSF1 promoter indicates a median TTR less than about 15 months.

17. A method for assessing non-small cell lung cancer (NSCLC) recurrence and survival in a subject, the method comprising detecting hypermethylation in a sample from the subject at position −1310 of the phosphatase and tensin homolog (PTEN) promoter, wherein methylation of position −1310 of the PTEN promoter indicates a median time to recurrence (TTR) less than about 27 months.

18. The method of claim 17, wherein methylation of position −1310 of the PTEN promoter indicates a shorter TTR in the subject compared to when position −1310 of the PTEN promoter is not methylated.

* * * * *

SEQUENCE LISTING

```
<160> NUMBER OF SEQ ID NOS: 29

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
ggtatttaty gggagatgtt tattggatag                                    30

<210> SEQ ID NO 2
<211> LENGTH: 24
<212> TYPE: DNA
<213> ORGANISM: Artificial Sequence
```

```
<220> FEATURE:
<223> OTHER INFORMATION: Synthetic primer

<400> SEQUENCE: 2 tcaccccgc ctctaaacta ctcc                                              24

<210> SEQ ID NO 3
<211> LENGTH: 254
<212> TYPE: DNA
<213> ORGANISM: Homo sapiens

<400> SEQUENCE: 3
atcgggagat gctcattgga cagtcacgtg acgggaccaa acctcccgag ggagcgaggc      60
aggtgcggtc acgtgacccg gcggcgctgc ggggcagcgg ccattttgcg gggcggccac    120
gtgaaggacg cacgttcagc ggggctctca cgtgacccgg gcgcgctgcg gccgcccgcg    180
cggacccggc gagaggcggc ggcgggagcg gcggtgatgg acgggtccgg ggagcagccc    240
agaggcgggg gtga                                                      254

<210> SEQ ID NO 4
<211> LENGTH: 28
<212> TYPE: DNA
<213> ORGANISM: Artificial sequence
<220> FEATURE:
<223> OTHER INFORMATION: Synthetic primer

<400> SEQUENCE: 4
attttagtaa ttttaggtta gagggtta                                         28

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
accacaacca atcaacaac                                                   19

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
atggttattt ttgtttagat gag                                              23

<210> SEQ ID NO 7
<211> LENGTH: 27
<212> TYPE: DNA
<213> ORGANISM: Artificial Sequence
<220> FEATURE:
<223> OTHER INFORMATION: Synthetic primer

<400> SEQUENCE: 7
gagggtagtt tagtaatgtg ttatagg                                          27

<210> SEQ ID NO 8
<211> LENGTH: 21
<212> TYPE: DNA
<213> ORGANISM: Artificial Sequence
<220> FEATURE:
```

```
<223> OTHER INFORMATION: Synthetic primer

<400> SEQUENCE: 8
cctcccaact accctaccaa a                                          21

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
atggttattt tgtttagat gag                                         23

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
atggttattt tgtttagat gag                                         23

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
accctaaaaa taaaaacatt ataa                                       24

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
atggttattt tgtttagat gag                                         23

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
ggatgtgggt gtttgtgtaa tta                                        23

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
caataataac ccctcaccct taa                                        23
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tttgtgtaat tagttttta                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
agtttggatt ttgggggagg                                         20

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
caactcaata aactcaaact cccc                                    24

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
gggttagttt tgtggttt                                           18

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
ggaattttgt agttgtttta ggtgaa                                  26

<210> SEQ ID NO 20
<211> LENGTH: 26
<212> TYPE: DNA
<213> ORGANISM: Artificial Sequence
<220> FEATURE:
<223> OTHER INFORMATION: Synthetic primer

<400> SEQUENCE: 20
tttaaaaaaa ccccaaccta ctaaac                                  26

<210> SEQ ID NO 21
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 21
aagaagtttt taaatttata tt                                              22

<210> SEQ ID NO 22
<211> LENGTH: 40
<212> TYPE: DNA
<213> ORGANISM: Homo sapiens

<400> SEQUENCE: 22
ygygtttatg ygaggtyggg tgggygggty gttagtttyg                           40

<210> SEQ ID NO 23
<211> LENGTH: 45
<212> TYPE: DNA
<213> ORGANISM: Homo sapiens

<400> SEQUENCE: 23
ggggygttyg ygtttygggy ggaygtattg gttttyggt yggyg                      45

<210> SEQ ID NO 24
<211> LENGTH: 46
<212> TYPE: DNA
<213> ORGANISM: Homo sapiens

<400> SEQUENCE: 24
yggtaygtty gtgaagtygt tatttagtta gtttgggggt taygag                    46

<210> SEQ ID NO 25
<211> LENGTH: 25
<212> TYPE: DNA
<213> ORGANISM: Homo sapiens

<400> SEQUENCE: 25
ygttttgygt ttygaygtty gyagg                                           25

<210> SEQ ID NO 26
<211> LENGTH: 88
<212> TYPE: DNA
<213> ORGANISM: Homo sapiens

<400> SEQUENCE: 26
ygygtagayg tygtttggta yggattttat tttttyggt tygtygyygg ttttttgg       60 tygttttttt tgttatttyg atttttttt                                       88

<210> SEQ ID NO 27
<211> LENGTH: 36
<212> TYPE: DNA
<213> ORGANISM: Homo sapiens

<400> SEQUENCE: 27
gggtggggyg gatygygtgy gttyggyggt tgygga                               36

<210> SEQ ID NO 28
<211> LENGTH: 43
<212> TYPE: DNA
<213> ORGANISM: Homo sapiens

<400> SEQUENCE: 28
agygttagtt tygatagygt tttttyggga ggttggttyg agt                       43

<210> SEQ ID NO 29
<211> LENGTH: 33
```

```
<212> TYPE: DNA
<213> ORGANISM: Homo sapiens

<400> SEQUENCE: 29
ygttyggtty gygtttgtta gygtttaaag tta                               33
```